US012637704B2

(12) United States Patent
Phadke et al.

(10) Patent No.: US 12,637,704 B2
(45) Date of Patent: May 26, 2026

(54) COMPOSITION AND METHOD FOR IMPROVING DETECTION OF BIOMOLECULES IN BIOFLUID SAMPLES

(71) Applicant: GenePath Diagnostics Inc., Ann Arbor, MI (US)

(72) Inventors: Nikhil Phadke, Ann Arbor, MI (US); Siddharth Anand, Ann Arbor, MI (US)

(73) Assignee: GenePath Diagnostics Inc., Ann Arbor, MI (US)

(*) Notice: Subject to any disclaimer, the term of this patent is extended or adjusted under 35 U.S.C. 154(b) by 1038 days.

(21) Appl. No.: 17/762,472

(22) PCT Filed: Sep. 23, 2020

(86) PCT No.: PCT/US2020/052252
§ 371 (c)(1),
(2) Date: Mar. 22, 2022

(87) PCT Pub. No.: WO2021/061797
PCT Pub. Date: Apr. 1, 2021

(65) Prior Publication Data
US 2022/0396824 A1 Dec. 15, 2022

Related U.S. Application Data

(60) Provisional application No. 62/904,773, filed on Sep. 24, 2019.

(51) Int. Cl.
*C12Q 1/6806* (2018.01)
*C12Q 1/70* (2006.01)
(52) U.S. Cl.
CPC ............. *C12Q 1/6806* (2013.01); *C12Q 1/70* (2013.01)
(58) Field of Classification Search
None
See application file for complete search history.

(56) References Cited

U.S. PATENT DOCUMENTS

| | | | |
|---|---|---|---|
| 5,334,499 A | 8/1994 | Burdick et al. | |
| 6,472,187 B1 | 10/2002 | Tonoike et al. | |
| 9,062,303 B2 | 6/2015 | Chen et al. | |
| 2011/0071031 A1* | 3/2011 | Khripin | C12N 15/101 |
| | | | 536/25.4 |
| 2013/0059292 A1 | 3/2013 | Kim et al. | |
| 2017/0007689 A1 | 1/2017 | Ciotti | |

| | | | |
|---|---|---|---|
| 2017/0342465 A1 | 11/2017 | Shum | |
| 2018/0002738 A1 | 1/2018 | Wang et al. | |
| 2018/0258476 A1 | 9/2018 | Koshinsky et al. | |
| 2022/0195502 A1 | 6/2022 | Phadke et al. | |
| 2022/0396824 A1 | 12/2022 | Phadke et al. | |

FOREIGN PATENT DOCUMENTS

| | | |
|---|---|---|
| EP | 0133671 | 3/1985 |
| EP | 0989192 | 3/2000 |
| WO | WO 2000/060120 | 10/2000 |
| WO | WO 2003/052101 | 6/2003 |
| WO | WO 2004/007755 | 1/2004 |
| WO | WO 2012/058638 | 5/2012 |
| WO | WO 2012/149188 | 11/2012 |
| WO | WO 2013/046033 | 4/2013 |
| WO | WO 2018/089978 | 5/2018 |

OTHER PUBLICATIONS

Thermo Fisher-LiCl: The Use of LiCl Precipitation for RNA Purification (https://www.thermofisher.com/us/en/home/references/ambion-tech-support/rna-isolation/general-articles/the-use-of-licl-precipitation-for-rna-purification.html)—downloadd Jul. 10, 2025. (Year: 2025).*
Gabert et al., "Standardization and quality control studies of 'real-time'quantitative reverse transcriptase polymerase chain reaction of fusion gene transcripts for residual disease detection in leukemia—a Europe Against Cancer program," Leukemia, Dec. 2003, 17(12):2318-57.
Pan et al., "Static and turnover kinetic measurement of protein biomarkers involved in triglyceride metabolism including apoB48 and apoA5 by LC/MS/MS [S]," Journal of Lipid Research, Jun. 1, 2014, 55(6):1179-87.
PCT International Preliminary Report on Patentability in International Appln. No. PCT/US2020/029622, Sep. 28, 2021, 15 pages.
PCT International Preliminary Report on Patentability in International Appln. No. PCT/US2020/052252, dated Mar. 15, 2022.
PCT International Search Report and Written Opinion in International Appln. No. PCT/US2020/029622, dated Aug. 20, 2020, 18 pages.
PCT International Search Report and Written Opinion in International Appln. No. PCT/US2020/052252, dated Jan. 6, 2021, 12 pages.
Salikhov, Efficient Algorithms and Data Structures for Indexing DNA Sequence Data, Universite Paris, Nov. 2017, 113 pages.

(Continued)

*Primary Examiner* — Nicole Kinsey White
*Assistant Examiner* — Ruixue Wang
(74) *Attorney, Agent, or Firm* — Fish & Richardson P.C.

(57) ABSTRACT

Provided herein are methods of detecting one or more nucleic acids in a biofluid sample. The methods include adding to the biofluid sample a composition comprising a sufficient amount of dextran sulphate to provide between 50 nM and 5 µM dextran sulphate when the composition is added to the biofluid sample.

10 Claims, 4 Drawing Sheets

(56)               References Cited

OTHER PUBLICATIONS

Wang et al., "Kynurenic acid as a ligand for orphan G protein-coupled receptor GPR35," Journal of Biological Chemistry, Aug. 4, 2006, 281(31):22021-8.

[No Author Listed], "Illumina Adapter Sequences," Illumina document 1000000002694, Feb. 2016, 38 pages.

Kennedy et al., "Detecting ultralow-frequency mutations by Duplex Sequencing," Nature protocols, Nov. 2014, 9(11):2586-606.

Kitson et al., "Nested metabarcode tagging: a robust tool for studying species interactions in ecology and evolution," BioRxiv, Jan. 2016, 1:035071, 12 pages.

EP Extended European Search Report in European Appln. No. 20867673.4, dated Sep. 29, 2023, 10 pages.

EP Extended Search Report in European Appln. No. 20794705.2, dated Jul. 28, 2023, 19 pages.

\* cited by examiner

COMPOSITION AND METHOD FOR IMPROVING DETECTION OF BIOMOLECULES IN BIOFLUID SAMPLES

CROSS-REFERENCE TO RELATED APPLICATIONS

This application is the National State of International Application No. PCT/US2020/052252, filed Sep. 23, 2020, which claims priority to U.S. Provisional Application No. 62/904,773, filed Sep. 24, 2019, the contents of which are incorporated herein by reference in their entireties.

TECHNICAL FIELD

The present disclosure relates to compositions and methods for improving detection of biomolecules in biofluid samples.

BACKGROUND

Biofluid samples are widely used for detecting and monitoring of a wide range of conditions and diseases. For example, biofluid samples can be collected and analyzed for the presence of biomolecules (biomarkers) to detect diseases or conditions, or monitor the progression of diseases or conditions. Urine is a useful biofluid because it can be obtained in a non-invasive manner, and analyzed for the presence of biomolecules to diagnose a wide range of diseases or conditions.

However, detection of certain biomolecules in biofluid samples can be challenging because biomolecules can degrade or break down over time in biofluid samples. For example, enzymes present in biofluid samples can rapidly destroy or degrade biomolecules. For this reason, detection of biomolecules such as nucleic acids in urine is challenging owing to the high nuclease activity in the urine, which causes rapid degradation and/or fragmentation over a short period. Considering that there often is a time lag between collection of biofluid samples from a subject and their testing or analysis for the presence of biomolecules of interest (e.g., because the biofluid samples have to be transported to a testing facility), detection of biomolecules that are typically rapidly degraded in biofluid samples remains a big challenge.

To mitigate the rapid degradation of biomolecules in biofluid samples, in some instances, biofluid samples need to be refrigerated or frozen to reduce enzymatic degradation of biomolecules between the time the biofluid samples are collected and analyzed, which presents additional logistical challenges.

In other instances, alternative methods are used to diagnose or monitor disease conditions, which can involve more invasive, inconvenient, and/or costly procedures involving removal of tissue or cell samples from subjects, such as biopsies, pap tests, or colposcopy examinations.

Hence, although urine samples can be easily obtained in a non-invasive manner for diagnosis of diseases and conditions, the testing and analysis of urine samples for the presence of biomolecules such as DNA and RNA is very time-sensitive, and thus remains a challenge.

SUMMARY

The present disclosure relates to methods for detecting a nucleic acid in a biofluid sample, the method comprising adding to the biofluid sample a composition comprising a sufficient amount of dextran sulphate to provide between 50 nM and 5 μM dextran sulphate when the composition is added to the biofluid sample.

The present disclosure also features methods for improving detection of biomolecules in biofluid samples by adding certain compositions to the biofluid samples, and compositions that can be used to improve detection of biomolecules in biofluid samples (e.g., by stabilizing the biomolecules) for a period after obtaining the biofluid samples.

In some aspects, the present disclosure relates to methods for improving detection of nucleic acid in a biofluid samples, the methods including adding to the biofluid samples compositions including a sufficient amount of dextran sulphate to provide between 50 nM and 5 μM dextran sulphate when the composition is added to the biofluid sample.

In some embodiments, the compositions further include: a buffer agent; a chelating agent; a sufficient amount of boric acid to provide between 4 mM and 400 mM boric acid when the composition is added to the biofluid sample; a sufficient amount of sodium citrate to provide between 4 mM and 400 mM sodium citrate when the composition is added to the biofluid sample; and a sufficient amount of lithium chloride to provide between 1 mM and 100 mM lithium chloride when the compositions are added to the biofluid sample.

In some embodiments, the buffer agents include a sufficient amount of Tris-HCl (pH 7.0) to provide between 8 mM and 800 mM Tris-HCl (pH 7.0) when the compositions containing the buffering agents are added to the biofluid samples.

In some embodiments, the chelating agents include a sufficient amount of ethylenediaminetetraacetic acid (EDTA) to provide between 0.4 mM and 40 mM EDTA when the compositions containing the chelating agents are added to the biofluid samples.

In some embodiments, the composition includes: a sufficient amount of Tris-HCl (pH 7.0) to provide about 80 mM Tris-HCl (pH 7.0) when the composition is added to the biofluid sample; a sufficient amount of EDTA to provide about 4 mM EDTA when the composition is added to the biofluid sample; a sufficient amount of boric acid to provide about 40 mM boric acid when the composition is added to the biofluid sample; a sufficient amount of sodium citrate to provide about 40 mM sodium citrate when the composition is added to the biofluid sample; a sufficient amount of dextran sulphate to provide about 500 nM dextran sulphate when the composition is added to the biofluid sample; and a sufficient amount of lithium chloride to provide about 10 mM lithium chloride when the composition is added to the biofluid sample.

In some embodiments, the composition further includes: a sufficient amount of aurintricarboxylic acid to provide between 1 mM and 100 mM aurintricarboxylic acid when the composition is added to the biofluid sample; a sufficient amount of polyvinylpyrrolidone to provide between 0.01% and 10% (w/v) polyvinylpyrrolidone when the composition is added to the biofluid sample; and a sufficient amount of Tris (2-carboxylethyl) phosphine to provide between 100 nM and 1 μM Tris (2-carboxylethyl) phosphine when the composition is added to the biofluid sample.

In some embodiments, the composition includes: a sufficient amount of aurintricarboxylic acid to provide about 10 mM aurintricarboxylic acid when the composition is added to the biofluid sample; a sufficient amount of polyvinylpyrrolidone to provide about 0.25% (w/v) polyvinylpyrrolidone when the composition is added to the biofluid sample; and a sufficient amount of Tris (2-carboxylethyl) phosphine to provide about 500 nM Tris (2-carboxylethyl) phosphine when the composition is added to the biofluid sample.

In some embodiments, the addition of the composition to the biofluid sample results in improved DNA or RNA detection in the biofluid sample, as measured by % amount of DNA or RNA detected after 3 or 7 days, compared to the amount of DNA or RNA detected at time 0, where the % amount of DNA or RNA detected after 3 or 7 days is at least 50%, at least 60%, at least 70%, at least 80%, at least 90%, at least 95%, at least 96%, at least 97%, at least 98%, at least 99%, or greater than 100% of the amount of DNA or RNA that is detected at time 0.

In some embodiments, the biofluid sample is urine.

In some embodiments, the biofluid sample includes fecal contaminant. In some embodiments, the composition is powder, a tablet, a gel, or an aqueous solution.

In some embodiments, the method further includes detecting or having detected, one or more target DNA or RNA sequence(s) in the biofluid sample after a period of time.

In some embodiments, the period of time is more than 1 hour, 1.5 hour, 2 hours, 3 hours, 4 hours, 5 hours, 6 hours, 7 hours, 8 hours, 9 hours, 10 hours, 11 hours, 12 hours, 18 hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, or 5 years.

In some embodiments, the biofluid sample is stored at a temperature greater than 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C., during the period of time.

In some embodiments, the target DNA or RNA is detected using next-generation sequencing (NGS), real-time PCR, or an isothermal amplification method.

In some embodiments, the one or more target DNA or RNA sequence(s) are DNA or RNA sequence(s) of an infectious agent.

In some embodiments, the infectious agent is a virus, a bacteria, or a fungus.

In some embodiments, the virus is Herpesviridae (Herpes simplex Viruses 1 and 2), Varicella zoster virus, Human herpes virus-6, Human herpes virus-7, Human herpes virus-8), Epstein barr virus, Adenovirus, Cytomegalovirus, Human papilloma virus, Enterovirus, Zika virus, Polyomaviruses such as BK virus, Coxsackie A viruses, Hepatitis viruses, Arbovirus, Parvovirus B19, Reovirus, Measles virus, Gastrointestinal viruses, Influenza, Parainfluenza, Mumps, Respiratory syncytial virus, Adenoviruses, Coronaviruses, Enteroviruses, Hemorrhagic fever viruses (such as Congo-Crimean hemorrhagic fever, Ebola virus, Hantavirus, Dengue, chikungunya, West Nile virus, Nipah virus, Yellow fever virus, Hepatitis A, Hepatitis B, Hepatitis C, Noroviruses, Rabies, Rhinovirus, or Birnaviruses (rotaviruses).

In some embodiments, the virus is a coronavirus. In some instances, the virus is SARS-CoV-1. In some instances, the virus is SARS-CoV-2. In some instances, the virus is Middle East Respiratory Syndrome (MERS).

In some embodiments, the bacteria is Mycobacteria, Serratia, Staphylococci, Streptococci, Klebsiella, Escherechia, Neisseria, Shigella, Salmonella, Helicobacteria, Listeria, Morganella, Pseudomonas, Acinetobacter, Bacteroides, Burkholderia, Clositridium, Enterobacteriaceae, Enterococcus, Stenotrophomonas. In certain instances, the infectious agent can be a fungus such as Entomophtoromycota (such as Basidiobolus and Conidiobolus), Ascomycota (such as Candida, Aspergillus, Non-Fumigatus Aspergilli, Fusarium, Pseudoallescheria, and Other Opportunistic, Ascomycetous Fungal Pathogens such as Blastomyces, Pneumocystis), Basdiomycota (such as Cryptococci), Mucorales (such as Mucor and Rhizopus), or Histoplasma.

In some embodiments, the fungus is Entomophtoromycota (such as Basidiobolus and Conidiobolus), Ascomycota (such as Candida, Aspergillus, Non-Fumigatus Aspergilli, Fusarium, Pseudoallescheria, and Other Opportunistic, Ascomycetous Fungal Pathogens such as Blastomyces, Pneumocystis), Basdiomycota (such as Cryptococci), Mucorales (such as Mucor and Rhizopus), or Histoplasma.

In some embodiments, the one or more target DNA sequence(s) are genomic DNA sequences or genomic DNA sequences containing at least one somatic mutation, of a subject from whom the biofluid sample is obtained.

In some embodiments, the composition is added to the biofluid sample within one hour after obtaining the biofluid sample from a subject.

In some aspects, the present disclosure relates to methods of treating a subject for a condition, the method including: obtaining or having obtained a biofluid sample from a subject; performing any of the methods for improving detection of nucleic acid in a biofluid samples described herein; determining or having determined the level of a nucleic acid in the biofluid sample, thereby providing a diagnosis for the condition; and treating or having treated the subject for the condition according to the diagnosis.

In some embodiments, the condition is a urinary tract infection, genital tract infection, renal infection, prostate cancer, or cervical cancer.

In some aspects, the present disclosure relates to aqueous solutions including: a biofluid sample; and between 50 nM and 5 μM dextran sulphate.

In some embodiments, the aqueous solutions described herein further including: a buffer; a chelating agent; between 4 mM and 400 mM boric acid; between 4 mM and 400 mM sodium citrate; and between 1 mM and 100 mM lithium chloride.

In some embodiments, the buffer includes between 8 mM and 800 mM Tris-HCl (pH 7.0).

In some embodiments, the chelating agent includes between 0.4 mM and 40 mM EDTA.

In some embodiments, the aqueous solution includes about 500 nM dextran sulphate.

In some embodiments, the aqueous solution includes: about 40 mM boric acid; about 40 mM sodium citrate; and about 10 mM lithium chloride.

In some embodiments, the aqueous solution includes about 80 mM Tris-HCl (pH 7.0).

In some embodiments, the aqueous solution includes about 4 mM EDTA.

In some embodiments, the aqueous solution further includes: between 1 mM and 100 mM aurintricarboxylic acid; between 0.01% and 10% (w/v) polyvinylpyrrolidone; and 100 nM and 1 μM Tris (2-carboxylethyl) phosphine.

In some embodiments, the aqueous solution includes: about 10 mM aurintricarboxylic acid; about 0.25% (w/v) polyvinylpyrrolidone; and about 500 nM Tris (2-carboxylethyl) phosphine.

In some aspects, the present disclosure relates to compositions including: a sufficient amount of Tris-HCl (pH 7.0) to provide between 8 mM and 800 mM Tris-HCl (pH 7.0) when the composition is added to a biofluid sample; a sufficient amount of EDTA to provide between 0.4 mM and 40 mM EDTA when the composition is added to the biofluid sample; a sufficient amount of boric acid to provide between 4 mM and 400 mM boric acid when the composition is added to the biofluid sample; a sufficient amount of sodium citrate to provide between 4 mM and 400 mM sodium citrate when the composition is added to the biofluid sample; a sufficient amount of dextran sulphate to provide between 50 nM and 5 µM dextran sulphate when the composition is added to the biofluid sample; and a sufficient amount of lithium chloride between 1 mM and 100 mM lithium chloride when the composition is added to the biofluid sample, where the addition of the composition to a biofluid sample results in stabilization of a nucleic acid in the biofluid sample.

In some embodiments, the compositions described herein further includes: a sufficient amount of aurintricarboxylic acid to provide between 1 mM and 100 mM aurintricarboxylic acid when the composition is added to the biofluid sample; a sufficient amount of polyvinylpyrrolidone to provide between 0.01% and 10% (w/v) polyvinylpyrrolidone when the composition is added to the biofluid sample; and a sufficient amount of Tris (2-carboxylethyl) phosphine to provide between 100 nM and 1 µM Tris (2-carboxylethyl) phosphine when the composition is added to the biofluid sample.

In some embodiments, the compositions described herein includes a sufficient amount of Tris-HCl (pH 7.0) to provide about 80 mM Tris-HCl (pH 7.0) when the composition is added to the biofluid sample; a sufficient amount of EDTA to provide about 4 mM EDTA when the composition is added to the biofluid sample; a sufficient amount of boric acid to provide about 40 mM boric acid when the composition is added to the biofluid sample; a sufficient amount of sodium citrate to provide about 40 mM sodium citrate when the composition is added to the biofluid sample; a sufficient amount of dextran sulphate to provide about 500 nM dextran sulphate when the composition is added to the biofluid sample; and a sufficient amount of lithium chloride to provide about 10 mM lithium chloride when the composition is added to the biofluid sample.

In some embodiments, the compositions described herein further includes: a sufficient amount of aurintricarboxylic to provide about 10 mM aurintricarboxylic acid when the composition is added to the biofluid sample; a sufficient amount of polyvinylpyrrolidone to provide about 0.25% (w/v) polyvinylpyrrolidone when the composition is added to the biofluid sample; and a sufficient amount of Tris (2-carboxylethyl) phosphine to provide about 500 nM Tris (2-carboxylethyl) phosphine when the composition is added to the biofluid sample.

In some aspects, the present disclosure relates to kits including: a sufficient amount of dextran sulphate to provide between 50 nM and 5 µM dextran sulphate when the dextran sulphate is added to a biofluid sample; and optionally further including one or more of: a sufficient amount of Tris-HCl (pH 7.0) to provide between 8 mM and 800 mM Tris-HCl (pH 7.0) when the Tris-HCl (pH 7.0) is added to the biofluid sample; a sufficient amount of EDTA to provide between 0.4 mM and 40 mM EDTA when the EDTA is added to the biofluid sample; a sufficient amount of boric acid to provide between 4 mM and 400 mM boric acid when the boric acid is added to the biofluid sample; a sufficient amount of sodium citrate to provide between 4 mM and 400 mM sodium citrate when the sodium citrate is added to the biofluid sample; a sufficient amount of lithium chloride to provide between 1 mM and 100 mM lithium chloride when the lithium chloride is added to the biofluid sample; a sufficient amount of aurintricarboxylic acid to provide between 1 mM and 100 mM aurintricarboxylic acid when the aurintricarboxylic acid is added to the biofluid sample; a sufficient amount of polyvinylpyrrolidone to provide between 0.01% and 10% (w/v) polyvinylpyrrolidone when the polyvinylpyrrolidone is added to the biofluid sample; and a sufficient amount of Tris (2-carboxylethyl) phosphine to provide between 100 nM and 1 µM Tris (2-carboxylethyl) phosphine when the Tris (2-carboxylethyl) phosphine is added to the biofluid sample.

In some embodiments, the kits described herein includes: a sufficient amount of dextran sulphate to provide about 500 nM dextran sulphate when the dextran sulphate is added to a biofluid sample; and optionally further including one or more of: a sufficient amount of Tris-HCl (pH 7.0) to provide about 80 mM Tris-HCl (pH 7.0) when the Tris-HCl (pH 7.0) is added to the biofluid sample; a sufficient amount of EDTA to provide about 4 mM EDTA when the EDTA is added to the biofluid sample; a sufficient amount of boric acid to provide about 40 mM boric acid when the boric acid is added to the biofluid sample; a sufficient amount of sodium citrate to provide about 40 mM sodium citrate when the sodium citrate is added to the biofluid sample; a sufficient amount of lithium chloride to provide about 10 mM lithium chloride when the lithium chloride is added to the biofluid sample; a sufficient amount of aurintricarboxylic acid to provide about 10 mM aurintricarboxylic acid when the aurintricarboxylic acid is added to the biofluid sample; a sufficient amount of polyvinylpyrrolidone to provide about 0.25% (w/v) polyvinylpyrrolidone when the polyvinylpyrrolidone is added to the biofluid sample; and a sufficient amount of Tris (2-carboxylethyl) phosphine to provide about 500 nM Tris (2-carboxylethyl) phosphine when the Tris (2-carboxylethyl) phosphine is added to the biofluid sample.

In some aspects, the present disclosure relates to devices for detecting a biomolecule in a biofluid sample, including a collection container for collecting a biofluid sample, where the collection container contains any of the compositions described herein, and optionally further including: (1) a processing module capable of lysing cells, enriching or separating the biomolecule, and/or amplifying the biomolecule; (2) a detection module capable of detecting the biomolecule; and/or (3) a readout module capable of providing information regarding the presence of absence of the biomolecule to a user.

In some embodiments, the biomolecule is a DNA or an RNA molecule having a specific sequence.

In some embodiments, the biomolecule is a DNA molecule having a sequence associated with HPV infection.

In some embodiments, the processing module is capable of amplifying the biomolecule using an isothermic DNA amplification method.

In some embodiments, the isothermic DNA amplification method is LAMP, HDA or RPA.

In some embodiments, the detection module is capable of detecting the presence of two or more distinct biomolecules.

In some embodiments, the two or more distinct biomolecules are each associated with two or more different types of HPV.

In some embodiments, the readout of the presence or the absence of each of the two or more distinct biomolecules are provided in a 2D macro-array or a 3D macro-array, where two or more distinct probes that each specifically binds to one of the two or more distinct biomolecules are immobilized on a 2D surface or a 3D structure.

In some embodiments, the detection module includes an RNA probe having a sequence that is complementary to the DNA molecule, and an antibody that is specific for the DNA-RNA hybrid that forms as a result of the RNA probe binding to the DNA molecule, and where the antibody is detected using a sandwich ELISA method.

In some embodiments, the steps of processing, detecting, and providing a readout are carried out by the device without an input from a healthcare professional.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

DETAILED DESCRIPTION

Figure 1:
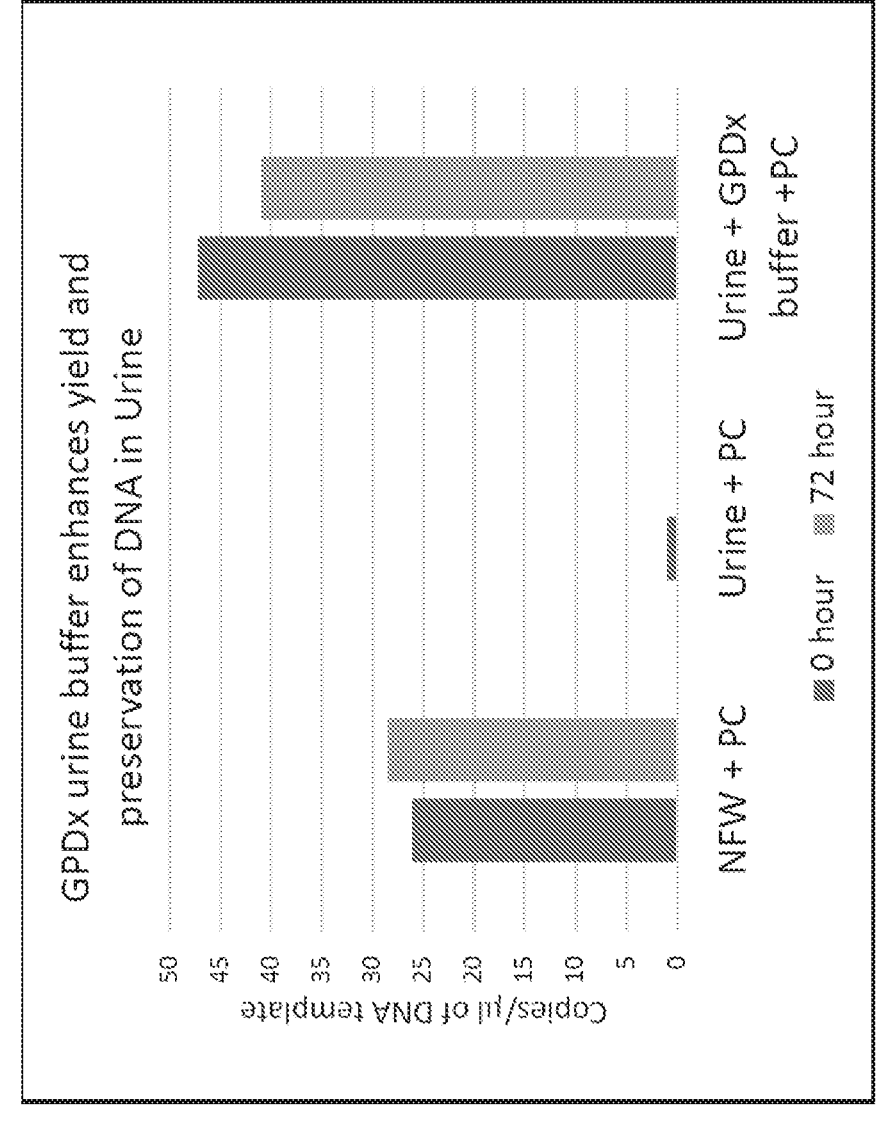
FIG. 1 is a bar graph showing the effects of adding Formulation A solution (indicated as GPDx) on detection of DNA in the urine samples 72 hours after collection.

The present disclosure is based on the discovery that addition of certain additives (or compositions) to biofluid samples can improve detection of biomolecules in biofluid samples. In certain instances, compositions described herein can be added to biofluid samples to improve detection of biomolecules such as DNA or RNA that are otherwise degraded or fragmented e.g., by enzymatic degradation. Adding certain compositions to biofluid samples can allow improved detection of biomolecules due, at least in part, to: (1) improvements in the detection sensitivity of the biomolecules in the biofluid samples; (2) improvements in the stability of the biomolecules in the biofluid samples; and/or (3) inhibition or reduction of enzymatic activities that otherwise would result in degradation of the biomolecules in the biofluid sample. Such improved detection of biomolecules in biofluid samples enables detection of biofluid samples at a time (e.g., a few minutes, a few hours, a few days, or a few weeks) after the biofluid samples are collected, and/or storage of collected biofluid samples at ambient temperature (i.e., without refrigerating or freezing the biofluid samples) between the time the biofluid samples are collected and the time the biofluid samples are analyzed to detect biomolecules.

This improved detection of biomolecules in biofluid samples is useful for diagnosing and/or monitoring diseases or conditions by allowing detection of certain biomolecules in biofluid samples a period of time after the biofluid samples are collected. For example, the compositions and methods described herein can provide new diagnostic methods that are less invasive, more convenient, less costly, more scalable, and/or provide more information about the diseases or conditions for which the biofluid samples are being analyzed. For example, improved detection of DNA or RNA in urine can enable diagnosis of cancers or sexually transmitted diseases, which traditionally required procedures such as invasive tissue biopsies, pap tests, urethral swabs, or colposcopy. Further, because certain biofluid samples, such as urine, can be collected at one site (e.g., a subject's home) and transported to another site for analysis (e.g., hospital or laboratory) without the need for refrigeration or freezing of the samples, the methods and compositions described herein can provide a more convenient, scalable, cost-effective, and/or widespread diagnostic options. Still further, the compositions and methods described herein, which enables more sensitive and/or robust detection of DNA or RNA in biofluid samples (e.g., urine), can be used in a range of diagnostics applications, including in diagnostics devices that can collect, enrich, process, and/or analyze the biofluid samples without the need for sending collected samples to a laboratory facility, thereby providing diagnosis information to subjects or healthcare professionals at the point-of-care facility.

Biofluid Samples

The biofluids as described herein can include biological fluids that can be obtained from subjects (e.g., a mammal such as a human) invasively using a needle or non-invasively by collecting excreted or secreted biofluid. For example, the biofluid can be blood that is obtained by accessing the subject's vein or artery using a needle, or the biofluid can be cerebrospinal fluid (CSF) which is obtained by lumbar puncture (i.e., spinal tap). In other instances, the biofluid sample can be amniotic fluid, synovial fluid, pleural fluid, or pericardial fluid, which can be obtained from a subject in an invasive manner.

In some instances, the biofluid samples can also be biological fluids that can be obtained from a subject by collecting excreted or secreted biofluid. For example, the biofluid can be urine, which can be collected as it is being excreted (via urination) by a subject. The biofluid can also be sweat, which can be collected as it is being excreted (via perspiration) by a subject. The biofluid can also be breast milk, which can be collected as it is being secreted from the subject.

The volume of biofluid samples that can be used in the methods described herein depends on the type of biofluid that is being collected. In some instances where urine is the biofluid sample collected, the volume of urine that is collected for analysis can be greater than about 0.01 mL, 0.05 mL, 0.1 mL, 0.2 mL, 0.3 mL, 0.4 mL, 0.5 mL, 0.6 mL, 0.7 mL, 0.8 mL, 0.9 mL, 1.0 mL, 25 mL, 50 mL, 75 mL, 100 mL, 150 mL, 200 mL, 250 mL, 300 mL, 350 mL, 400 mL, 450 mL, or 500 mL. In some instances where urine is collected as biofluid samples, the volume of urine that is collected for analysis can be less than about 25 mL, 50 mL, 75 mL, 100 mL, 150 mL, 200 mL, 250 mL, 300 mL, 350 mL, 400 mL, 450 mL, 500 mL, 600 mL, or 700 mL.

In other instances, the volume of urine that is collected for analysis can be less than about 0.01 mL, 0.05 mL, 0.1 mL, 0.2 mL, 0.3 mL, 0.4 mL, 0.5 mL, 0.6 mL, 0.7 mL, 0.8 mL, 0.9 mL, 1.0 mL, 25 mL, 50 mL, 75 mL, 100 mL, 150 mL, 200 mL, 250 mL, 300 mL, 350 mL, 400 mL, 450 mL, or 500 mL.

In some instances, collecting and analyzing larger volumes of biofluid samples is advantageous, because the total amount of biomolecules (e.g., DNA or RNA) present in the biofluid sample can be proportional to the total volume collected. Further biosamples having larger volumes can be enriched for the biomolecules of interest, e.g., by using subtrates for capturing the biomolecules of interest and/or filtering the biosamples to concentrate the biomolecules of interest while reducing the total volume of biofluid sample, prior to analysis. In these instances, a larger amount of biomolecules can be collected from larger volumes of biofluid samples for analysis, which can increase detection sensitivity.

Biomolecules

Biomolecules (or biological molecules) are substances that are produced by cells and living organisms. In some instances, biomolecules can be nucleic acids (e.g., RNA or DNA) or proteins.

In instances where the biomolecule is RNA, the RNA can be mRNA, hnRNA, lncRNA, siRNA, circRNA, miRNA, or other species of RNA that may be useful in diagnosis or monitoring of a disease or a condition (e.g., PCA3, HOTAIR, ANRIL, MALAT1, or GAS5 lncRNA for diagnosis or monitoring of prostate cancer). The RNA can also include transcripts (e.g., mRNA or pre-mRNA), for example, those transcripts containing non-host DNA sequences (e.g., DNA sequences of pathogens such as HPV) that has been incorporated into a host genome, or RNA sequences corresponding to a viral or bacterial DNA or RNA.

The presence of certain biomolecules (e.g., biomarkers) can be used to diagnose or monitor a condition or a disease. For example, detection of nucleic acid molecules (e.g., DNA or RNA) having sequences specific for a pathogen can indicate an infection. As another instance, presence of certain gene mutations can indicate an increased risk for certain diseases (e.g., cancer) or conditions.

In certain instances where the biomolecules being detected are DNA or RNA, sequence information of the DNA or RNA being detected can provide information that may otherwise be unavailable by other diagnostic methods (e.g., tissue biopsies, imaging investigations, or visual examination of affected tissues). For example, in instances where the DNA or RNA being detected are those corresponding to the genomic DNA or RNA of a pathogen, different strains, subtypes, or subspecies of the pathogen can be definitively identified based on the sequence information.

Progression of a condition or a disease can also be monitored by analyzing biomolecules in biofluid samples over time to detect, for example, any changes in the levels or presence of biomolecules in biofluid samples.

Various methods for detecting biomolecules in biofluid samples are known in the art. For example, nucleic acids (e.g., DNA or RNA) having specific sequences can be detected and/or quantified by northern or southern blotting, quantitative PCR, quantitative RT-PCR, or next-generation sequencing (NGS).

Compositions for Improving Detection of Biomolecules in Biofluid Samples

Composition Format

In some instances, the present disclosure relates to compositions that contain one or more of the components described herein, that can be added to biofluid samples in various forms, such as powder, gel capsule, aqueous solution, or tablet. For example, a composition described herein can be in a concentrated buffer solution form (e.g., 2×, 5×, 10×, 20×, or 100× buffer solution) that can be added to biofluid samples in a specific ratio (e.g., buffer solution: biofluid ratio of 1:1, 1:4, 1:9, 1:19, or 1:99) to result in specific concentrations of the constituents of the compositions when the composition is added to the biofluid samples.

As another example, a composition described herein can be in a powder form, a tablet form, or a gel capsule form, which can be added to biofluid samples (e.g., a specific volume of biofluid samples) to result in specific concentrations or range of concentrations of the constituents of the compositions when the composition is added to the biofluid samples.

The specific composition format can be chosen so that an appropriate amount of a composition described herein can readily be added to biofluid samples at the time of biofluid sample collection, or soon after biofluid sample collection to minimize degradation of biomolecules in the biofluid samples.

In some instances, the compositions in various forms can be provided in biofluid sample collection containers (e.g., urine sample collecting containers), such that the biofluid samples (e.g., a specified volume of the biofluid samples) can be collected or added directly into the biofluid sample collection containers to result in specific final concentrations of the constituents of the compositions.

Dextran Sulphate

In some instances, the present disclosure is based on the discovery that addition of compositions containing dextran sulphate to biofluid samples can improve detection of certain biomolecules such as nucleic acids (DNA or RNA) in the biofluid samples. This improved detection of nucleic acids can be attributed, at least in part, to improved stability of the biomolecules in the biofluid samples (e.g., increased half-life of nucleic acids or resistance to degradation) and/or improved detection sensitivity of the biomolecules in the biofluid samples (e.g., increased sensitivity of DNA or RNA detection by PCR-based detection methods). For instance, dextran sulphate can inhibit enzymes (e.g., nucleases) that may be present in biofluids, thereby preventing or reducing degradation or fragmentation of biomolecules (e.g., DNA or RNA) present in biofluid samples. Dextran sulphate can also improve amplification of DNA molecules in PCR reactions, for example, by (1) reversibly inhibits polymerases and nucleases in a temperature dependent manner, wherein the nuclease inhibition at the collection temperature should protect nucleic acids from nuclease degradation, and (2) in a PCR reaction, "hot-starting" the polymerase which improves the yield of PCR, thereby apparently creating an 'enhancement' effect, thereby increasing detection sensitivity.

Dextran sulphate is a polymer including glucose, and can vary in length (e.g., between 3-2000 kD). In certain instances, the compositions described herein can include dextran sulphate that has an average molecular weight of between about 3 kD and 5 kD, 5 kD and 10 kD, 10 kD and 15 kD, 15 kD and 20 kD, 20 kD and 25 kD, 25 kD and 30 kD, 30 kD and 35 kD, 35 kD and 40 kD, 40 kD and 45 kD, 45 kD and 50 kD, 50 kD and 60 kD, 60 kD and 70 kD, 70 kD and 80 kD, 80 kD and 90 kD, 90 kD and 100 kD, 100 kD and 125 kD, 125 kD and 150 kD, 150 kD and 175 kD, 175 kD and 200 kD, 200 kD and 250 kD, 250 kD and 300 kD, 300 kD and 350 kD, 350 kD and 400 kD, 400 kD and 450 kD, 450 kD and 500 kD, 500 kD and 600 kD, 600 kD and 700 kD, 700 kD and 800 kD, 800 kD and 900 kD, 900 kD and 1000 kD, 1000 kD and 1100 kD, 1100 kD and 1200 kD, 1200 kD and 1300 kD, 1300 kD and 1400 kD, 1400 kD and 1500 kD, 1500 kD and 1600 kD, 1600 kD and 1700 kD, 1700 kD and 1800 kD, 1800 kD and 1900 kD, 1900 kD and 2000 kD, or greater than 2000 kD.

In certain other instances, the average molecular weight of dextran sulphate can be greater than about 3 kD, 4 kD, 5 kD, 6 kD, 7 kD, 8 kD, 9 kD, 10 kD, 11 kD, 12 kD, 13 kD, 14 kD, 15 kD, 16 kD, 17 kD, 18 kD, 19 kD, 20 kD, 25 kD, 30 kD, 35 kD, 40 kD, 45 kD, 50 kD, 60 kD, 70 kD, 80 kD, 90 kD, 100 kD, 120 kD, 140 kD, 160 kD, 180 kD, 200 kD, 250 kD, 300 kD, 350 kD, 400 kD, 450 kD, 500 kD, 600 kD, 700 kD, 800 kD, 900 kD, 1000 kD, 1100 kD, 1200 kD, 1300 kD, 1400 kD, 1500 kD, 1600 kD, 1700 kD, 1800 kD, 1900 kD, or 2000 kD.

In certain other instances, the average molecular weight of dextran sulphate can be less than about 3 kD, 4 kD, 5 kD, 6 kD, 7 kD, 8 kD, 9 kD, 10 kD, 11 kD, 12 kD, 13 kD, 14 kD, 15 kD, 16 kD, 17 kD, 18 kD, 19 kD, 20 kD, 25 kD, 30 kD, 35 kD, 40 kD, 45 kD, 50 kD, 60 kD, 70 kD, 80 kD, 90 kD, 100 kD, 120 kD, 140 kD, 160 kD, 180 kD, 200 kD, 250 kD, 300 kD, 350 kD, 400 kD, 450 kD, 500 kD, 600 kD, 700 kD, 800 kD, 900 kD, 1000 kD, 1100 kD, 1200 kD, 1300 kD, 1400 kD, 1500 kD, 1600 kD, 1700 kD, 1800 kD, 1900 kD, or 2000 kD.

In some instances, the amount of dextran sulphate that is present in a composition described herein can be an amount that is sufficient to provide a final concentration of between about 5 nM and 50 μM (e.g., between about 5 nM and 50 nM, 50 nM and 500 nM, 500 nM and 5 μM, 5 μM and 50 μM) when the composition is added to the biofluid samples. For example, the amount of dextran sulphate that is present in a composition described herein can be an amount sufficient to provide a final concentration of about 5 nM, 10 nM, 15 nM, 20 nM, 25 nM, 30 nM, 35 nM, 40 nM, 45 nM, 50 nM, 60 nM, 70 nM, 80 nM, 90 nM, 100 nM, 125 nM, 150 nM, 175 nM, 200 nM, 250 nM, 300 nM, 350 nM, 400 nM, 450 nM, 500 nM, 600 nM, 700 nM, 800 nM, 900 nM, 1.0 μM, 1.1 μM, 1.2 μM, 1.3 μM, 1.4 μM, 1.5 μM, 1.6 μM, 1.7 μM, 1.8 μM, 1.9 μM, 2.0 μM, 2.25 μM, 2.5 μM, 2.75 μM, 3.0 μM, 4.0 μM, 5.0 μM, 6.0 μM, 7.0 μM, 8.0 μM, 9.0 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, or 50 μM, when the composition is added to the biofluid samples.

In some instances, the amount of dextran sulphate that is present in a composition described herein can be an amount sufficient to provide a final concentration of greater than about 5 nM, 10 nM, 15 nM, 20 nM, 25 nM, 30 nM, 35 nM, 40 nM, 45 nM, 50 nM, 60 nM, 70 nM, 80 nM, 90 nM, 100 nM, 125 nM, 150 nM, 175 nM, 200 nM, 250 nM, 300 nM, 350 nM, 400 nM, 450 nM, 500 nM, 600 nM, 700 nM, 800 nM, 900 nM, 1.0 μM, 1.1 μM, 1.2 μM, 1.3 μM, 1.4 μM, 1.5 μM, 1.6 μM, 1.7 μM, 1.8 μM, 1.9 μM, 2.0 μM, 2.25 μM, 2.5 μM, 2.75 μM, 3.0 μM, 4.0 μM, 5.0 μM, 6.0 μM, 7.0 μM, 8.0 μM, 9.0 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, or 50 μM, when the composition is added to the biofluid samples.

In some instances, the amount of dextran sulphate that is present in a composition described herein can be an amount sufficient to provide a final concentration of less than about 5 nM, 10 nM, 15 nM, 20 nM, 25 nM, 30 nM, 35 nM, 40 nM, 45 nM, 50 nM, 60 nM, 70 nM, 80 nM, 90 nM, 100 nM, 125 nM, 150 nM, 175 nM, 200 nM, 250 nM, 300 nM, 350 nM, 400 nM, 450 nM, 500 nM, 600 nM, 700 nM, 800 nM, 900 nM, 1.0 μM, 1.1 μM, 1.2 μM, 1.3 μM, 1.4 μM, 1.5 μM, 1.6 μM, 1.7 μM, 1.8 μM, 1.9 μM, 2.0 μM, 2.25 μM, 2.5 μM, 2.75 μM, 3.0 μM, 4.0 μM, 5.0 μM, 6.0 μM, 7.0 μM, 8.0 μM, 9.0 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, or 50 μM, when the composition is added to the biofluid samples.

In some instances, the dextran sulphate that is present in the compositions described herein can be dextran sulphate in a salt form (e.g., dextran sulphate sodium or dextran sulphate potassium salt).

Buffering Agents

In certain instances, the compositions described herein can contain one or more buffering agent(s). Buffering agents can maintain the acidity (pH) of the biofluid samples, or prevent a rapid change in pH.

In some instances, the buffering agent(s) present in the compositions described herein can include Tris-HCl (pH 7.0). In some embodiments, the amount of buffering agent (e.g., Tris-HCl (pH 7.0)) that is present in the compositions described herein is an amount that is sufficient to provide a final concentration of between about 800 μM and 8M of the buffering agent (e.g., Tris-HCl (pH 7.0)) (e.g., between about 800 μM and 8 mM, 8 mM and 80 mM, 80 mM and 800 mM, or 800 mM and 8.0 M) when the composition is added to the biofluid samples. For example, the amount of buffering agent (e.g., Tris-HCl (pH 7.0)) that is present in the compositions described herein can be an amount sufficient to provide a final concentration of about 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, 1.0 M, 1.1 M, 1.2 M, 1.3 M, 1.4 M, 1.5 M, 1.6 M, 1.7 M, 1.8 M, 1.9 M, 2.0 M, 2.5 M, 3.0 M, 3.5 M, 4.0 M, 4.5 M, 5.0 M, 5.5 M, 6.0 M, 6.5 M, 7.0 M, 7.5 M, or 8.0 M of the buffering agent (e.g., Tris-HCl (pH 7.0)), when the composition is added to the biofluid samples.

In other instances, the amount of buffering agent (e.g., Tris-HCl (pH 7.0)) that is present in the compositions described herein can be an amount sufficient to provide a final concentration of greater than about 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, 1.0 M, 1.1 M, 1.2 M, 1.3 M, 1.4 M, 1.5 M, 1.6 M, 1.7 M, 1.8 M, 1.9 M, 2.0 M, 2.5 M, 3.0 M, 3.5 M, 4.0 M, 4.5 M, 5.0 M, 5.5 M, 6.0 M, 6.5

M, 7.0 M, 7.5 M, or 8.0 M of the buffering agent (e.g., Tris-HCl (pH 7.0)), when the composition is added to the biofluid samples.

In yet other instances, the amount of buffering agent (e.g., Tris-HCl (pH 7.0)) that is present in the compositions described herein can be an amount sufficient to provide a final concentration of less than about 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, 1.0 M, 1.1 M, 1.2 M, 1.3 M, 1.4 M, 1.5 M, 1.6 M, 1.7 M, 1.8 M, 1.9 M, 2.0 M, 2.5 M, 3.0 M, 3.5 M, 4.0 M, 4.5 M, 5.0 M, 5.5 M, 6.0 M, 6.5 M, 7.0 M, 7.5 M, or 8.0 M of the buffering agent (e.g., Tris-HCl (pH 7.0)), when the composition is added to the biofluid samples.

In some instances, the buffering agent that is present in the compositions described herein can include other known buffer agents, e.g., Bicine, Bis-Tris, MOPS, MOPSO, MOBS, HEPES, PIPES, Tricine, MES, ADA, or ACES.

Chelating Agent

In certain instances, the present disclosure is related to compositions described herein can include one or more chelating agent(s). In certain instances, the chelating agent (s) present in the compositions described herein can include ethylenediaminetetraacetic acid (EDTA). In some instances, the amount of a chelating agent (e.g., EDTA) that is present in the compositions described herein is an amount that is sufficient to provide a final concentration of between about 40 μM and 400 mM of the chelating agent (e.g., EDTA) (e.g., between about 40 μM and 400 μM, 400 μM and 4 mM, 4 mM and 40 mM, or 40 mM and 400 mM), when the composition is added to the biofluid samples. For example, the amount of a chelating agent (e.g., EDTA) that is present in a composition described herein can be an amount suffi-cient to provide a final concentration of about 40 μM, 45 μM, 50 μM, 55 μM, 60 μM, 65 μM, 70 μM, 75 μM, 80 μM, 85 μM, 90 μM, 95 μM, 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, or 400 mM of the chelating agent (e.g., EDTA), when the composition is added to the biofluid samples.

In some instances, the amount of a chelating agent (e.g., EDTA) that is present in a composition described herein can be an amount sufficient to provide a final concentration of greater than about 40 μM, 45 μM, 50 μM, 55 μM, 60 μM, 65 μM, 70 μM, 75 μM, 80 μM, 85 μM, 90 μM, 95 μM, 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, or 400 mM of the chelating agent (e.g., EDTA), when the composition is added to the biofluid samples.

In some instances, the amount of a chelating agent (e.g., EDTA) that is present in a composition described herein can be an amount sufficient to provide a final concentration of less than about 40 μM, 45 μM, 50 μM, 55 μM, 60 μM, 65 μM, 70 μM, 75 μM, 80 μM, 85 μM, 90 μM, 95 μM, 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, or 400 mM of the chelating agent (e.g., EDTA), when the composition is added to the biofluid samples.

In some instances, the chelating agent that is present in the compositions described herein can include other known chelating agents, e.g., EGTA, Citric acid, DTPA (diethytri-aminepentaacetic acid)/Pentetic acid, Nitrilotriaceticacid (NTA), or Glycine.

Salts, Acid Salts, Weak Acids, Reducing Agents, and Other Compounds Commonly Used in Buffer Solutions In certain instances, the present disclosure is related to compositions that contain one or more salt(s), one or more acid salt(s), one or more weak acid(s), one or more reducing agent(s) and/or one or more other compound(s) commonly used in buffer solutions.

Boric Acid

In some instances, the compositions described herein can include boric acid. The amount of boric acid that can be present in a composition described herein is an amount that is sufficient to provide a final concentration of between about 400 μM to 4.0 M boric acid (e.g., between about 400 μM to 4 mM, 4 mM to 40 mM, 40 mM to 400 mM, or 400 mM to 4.0 M) when the composition is added to the biofluid samples.

For example, the amount of boric acid present in a composition described herein can be an amount sufficient to provide a final concentration of about 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, 1.0 M, 1.1 M, 1.2 M, 1.3 M, 1.4 M, 1.5 M, 1.6 M, 1.7 M, 1.8 M, 1.9 M, 2.0 M, 2.5 M, 3.0 M, 3.5 M, or 4.0 M boric acid, when the composition is added to biofluid samples.

In some instances, the amount of boric acid present in a composition described herein can be an amount sufficient to provide a final concentration of greater than about 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, 1.0 M, 1.1 M, 1.2 M, 1.3 M, 1.4M, 1.5M, 1.6M, 1.7M, 1.8M, 1.9 M, 2.0 M, 2.5 M, 3.0 M, 3.5 M, or 4.0 M boric acid, when the composition is added to biofluid samples.

In some instances, the amount of boric acid present in a composition described herein can be an amount sufficient to provide a final concentration of less than about 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, 1.0 M, 1.1 M, 1.2 M, 1.3 M, 1.4 M, 1.5 M, 1.6 M, 1.7 M, 1.8 M, 1.9 M, 2.0 M, 2.5 M, 3.0 M, 3.5 M, or 4.0 M boric acid, when the composition is added to biofluid samples.

Sodium Citrate

In certain instances, the compositions described herein can include sodium citrate. The amount of sodium citrate that can be present in a composition described herein is an amount that is sufficient to provide a final concentration of between about 400 μM to 4.0 M sodium citrate (e.g., between about 400 μM to 4 mM, 4 mM to 40 mM, 40 mM to 400 mM, or 400 mM to 4.0 M) when the composition is added to biofluid samples.

For example, the amount of sodium citrate present in a composition described herein can be an amount sufficient to provide a final concentration of about 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, 1.0 M, 1.1 M, 1.2 M, 1.3 M, 1.4 M, 1.5 M, 1.6 M, 1.7 M, 1.8 M, 1.9 M, 2.0 M, 2.5 M, 3.0 M, 3.5 M, or 4.0 M sodium citrate, when the composition is added to biofluid samples.

In some instances, the amount of sodium citrate present in a composition described herein can be an amount sufficient to provide a final concentration of greater than about 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, 1.0 M, 1.1 M, 1.2 M, 1.3 M, 1.4 M, 1.5 M, 1.6 M, 1.7 M, 1.8 M, 1.9 M, 2.0 M, 2.5 M, 3.0 M, 3.5 M, or 4.0 M sodium citrate, when the composition is added to biofluid samples.

In some instances, the amount of sodium citrate present in a composition described herein can be an amount sufficient to provide a final concentration of less than about 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, 1.0 M, 1.1 M, 1.2 M, 1.3 M, 1.4 M, 1.5 M, 1.6 M, 1.7 M, 1.8 M, 1.9 M, 2.0 M, 2.5 M, 3.0 M, 3.5 M, or 4.0 M sodium citrate, when the composition is added to biofluid samples.

Lithium Chloride

In certain instances, the compositions described herein can include lithium chloride. In some instances, the amount of lithium chloride that is present in a composition described herein is an amount that is sufficient to provide a final concentration of between about 100 μM and about 1.0 M lithium chloride (e.g., between about 100 μM about 1 mM, 1 mM and 10 mM, 10 mM and 100 mM, or 100 mM and 1.0 M) when the composition is added to biofluid samples.

For example, the amount of lithium chloride present in a composition described herein can be an amount sufficient to provide a final concentration of about 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, or 1.0 M lithium chloride, when the composition is added to biofluid samples.

In some instances, the amount of lithium chloride present in a composition described herein can be an amount sufficient to provide a final concentration of greater than about 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, or 1.0 M lithium chloride, when the composition is added to biofluid samples.

In some instances, the amount of lithium chloride present in a composition described herein can be an amount sufficient to provide a final concentration of less than about 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, or 1.0 M lithium chloride, when the composition is added to biofluid samples.

Aurintricarboxylic Acid

In certain instances (e.g., in instances where the composition is being added to biofluid samples that have, or is suspected of having fecal contaminants), the compositions described herein can include aurintricarboxylic acid. In some instances, the amount of aurintricarboxylic acid that is present in a composition described herein is an amount that is sufficient to provide a final concentration of between about 100 μM and about 1.0 M aurintricarboxylic acid (e.g., between about 100 μM and 1 mM, 1 mM and 10 mM, 10 mM and 100 mM, or 100 mM and 1.0 M) when the composition is added to biofluid samples.

For example, the amount of aurintricarboxylic acid present in a composition described herein can be an amount sufficient to provide a final concentration of about 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, or 1.0 M aurintricarboxylic acid, when the composition is added to biofluid samples.

In some instances, the amount of aurintricarboxylic acid present in a composition described herein can be an amount sufficient to provide a final concentration of greater than about 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, or 1.0 M aurintricarboxylic acid, when the composition is added to biofluid samples.

In some instances, the amount of aurintricarboxylic acid present in a composition described herein can be an amount sufficient to provide a final concentration of less than about 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, or 1.0 M aurintricarboxylic acid, when the composition is added to biofluid samples.

Polyvinylpyrrolidone

In certain instances (e.g., in instances where the composition is being added to biofluid samples that have, or is suspected of having fecal contaminants), the compositions described herein can include polyvinylpyrrolidone. In some instances, the amount of polyvinylpyrrolidone that is present in a composition described herein is an amount that is sufficient to provide a final concentration of between about 0.01% (w/v) and 1.0% (w/v) polyvinylpyrrolidone (e.g., between about 0.01% and 0.05%, 0.05% and 0.1%, 0.1% and 0.5%, or 0.5% and 1.0%) when the composition is added to biofluid samples.

For example, the amount of polyvinylpyrrolidone present in a composition described herein can be an amount sufficient to provide a final concentration of about 0.01% (w/v), 0.02% (w/v), 0.03% (w/v), 0.04% (w/v), 0.05% (w/v), 0.06% (w/v), 0.07% (w/v), 0.08% (w/v), 0.09% (w/v), 0.1% (w/v), 0.125% (w/v), 0.15% (w/v), 0.175% (w/v), 0.2% (w/v), 0.225% (w/v), 0.25% (w/v), 0.275% (w/v), 0.3% (w/v), 0.35% (w/v), 0.40% (w/v), 0.45% (w/v), 0.5% (w/v), 0.6% (w/v), 0.7% (w/v), 0.8% (w/v), 0.9% (w/v), 1.0% (w/v), 2.0% (w/v), 3.0% (w/v), 4.0% (w/v), 5.0% (w/v), 6.0% (w/v), 7.0% (w/v), 8.0% (w/v), 9.0% (w/v), or 10% (w/v) polyvinylpyrrolidone, when the composition is added to biofluid samples.

In some instances, the amount of polyvinylpyrrolidone present in a composition described herein can be an amount sufficient to provide a final concentration of greater than about 0.01% (w/v), 0.02% (w/v), 0.03% (w/v), 0.04% (w/v), 0.05% (w/v), 0.06% (w/v), 0.07% (w/v), 0.08% (w/v), 0.09% (w/v), 0.1% (w/v), 0.125% (w/v), 0.15% (w/v), 0.175% (w/v), 0.2% (w/v), 0.225% (w/v), 0.25% (w/v), 0.275% (w/v), 0.3% (w/v), 0.35% (w/v), 0.40% (w/v), 0.45% (w/v), 0.5% (w/v), 0.6% (w/v), 0.7% (w/v), 0.8% (w/v), 0.9% (w/v), 1.0% (w/v), 2.0% (w/v), 3.0% (w/v), 4.0% (w/v), 5.0% (w/v), 6.0% (w/v), 7.0% (w/v), 8.0% (w/v), 9.0% (w/v), or 10% (w/v) polyvinylpyrrolidone, when the composition is added to biofluid samples.

In some instances, the amount of polyvinylpyrrolidone present in a composition described herein can be an amount sufficient to provide a final concentration of less than about 0.01% (w/v), 0.02% (w/v), 0.03% (w/v), 0.04% (w/v), 0.05% (w/v), 0.06% (w/v), 0.07% (w/v), 0.08% (w/v), 0.09% (w/v), 0.1% (w/v), 0.125% (w/v), 0.15% (w/v), 0.175% (w/v), 0.2% (w/v), 0.225% (w/v), 0.25% (w/v), 0.275% (w/v), 0.3% (w/v), 0.35% (w/v), 0.40% (w/v), 0.45% (w/v), 0.5% (w/v), 0.6% (w/v), 0.7% (w/v), 0.8% (w/v), 0.9% (w/v), 1.0% (w/v), 2.0% (w/v), 3.0% (w/v), 4.0% (w/v), 5.0% (w/v), 6.0% (w/v), 7.0% (w/v), 8.0% (w/v), 9.0% (w/v), or 10% (w/v) polyvinylpyrrolidone, when the composition is added to biofluid samples.

Tris (2-carboxylethyl) phosphine

In certain instances (e.g., in instances where the composition is being added to biofluid samples that have, or is suspected of having fecal contaminants), the compositions described herein can include Tris (2-carboxylethyl) phosphine. In some instances, the amount of Tris (2-carboxylethyl) phosphine that is present in a composition described herein is an amount that is sufficient to provide a final concentration of between about 100 μM and about 1.0 M Tris (2-carboxylethyl) phosphine (e.g., between about 100

μM about 1 mM, 1 mM and 10 mM, 10 mM and 100 mM, or 100 mM and 1.0 M) when the composition is added to biofluid samples.

For example, the amount of Tris (2-carboxylethyl) phosphine present in a composition described herein can be an amount sufficient to provide a final concentration of about 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, or 1.0 M Tris (2-carboxylethyl) phosphine, when the composition is added to biofluid samples.

In some instances, the amount of Tris (2-carboxylethyl) phosphine present in a composition described herein can be an amount sufficient to provide a final concentration of greater than about 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, or 1.0 M Tris (2-carboxylethyl) phosphine, when the composition is added to biofluid samples.

In some instances, the amount of Tris (2-carboxylethyl) phosphine present in a composition described herein can be an amount sufficient to provide a final concentration of less than about 100 μM, 110 μM, 120 μM, 130 μM, 140 μM, 150 μM, 160 μM, 170 μM, 180 μM, 190 μM, 200 μM, 225 μM, 250 μM, 275 μM, 300 μM, 325 μM, 350 μM, 375 μM, 400 μM, 450 μM, 500 μM, 600 μM, 700 μM, 800 μM, 900 μM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.0 mM, 4.5 mM, 5.0 mM, 6.0 mM, 7.0 mM, 8.0 mM, 9.0 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 250 mM, 300 mM, 350 mM, 400 mM, 450 mM, 500 mM, 600 mM, 700 mM, 800 mM, 900 mM, or 1.0 M Tris (2-carboxylethyl) phosphine, when the composition is added to biofluid samples.

Exemplary Final Concentrations of Various
Components of Composition

In certain embodiments, the composition can contain sufficient amounts of components to provide a final concentration of between about 50 nM and 5 µM dextran sulphate, and optionally also provide a final concentration of between about 8 mM and 800 mM Tris-HCl (pH 7.0), 0.4 mM and 40 mM EDTA, 4 mM and 400 mM boric acid, 4 mM and 400 mM sodium citrate, 1 mM and 100 mM lithium chloride, 1 mM and 100 mM aurintricarboxylic acid, 0.01% and 10% (w/v) polyvinylpyrrolidone, and/or 100 nM and 1 µM Tris (2-carboxylethyl) phosphine.

In some embodiments, the composition can contain sufficient amounts of components to provide a final concentration of about 500 nM dextran sulphate, and optionally also provide a final concentration of about 80 mM Tris-HCl (pH 7.0), 4 mM EDTA, 40 mM boric acid, 40 mM sodium citrate, 10 mM lithium chloride, 10 mM aurintricarboxylic acid, 0.25% (w/v) polyvinylpyrrolidone, and/or 500 nM Tris (2-carboxylethyl) phosphine.

Other Compounds Commonly Used in Buffers

In some instances, other components (or compounds) that are commonly used in buffers can be present in the compositions described herein, for example, reducing agents such as TCEP, Dithiothretol, Dithioerythritol, L-glutathione (GSH), or beta mercaptoethanol.

Methods for Detecting Biomolecules in Biofluid
Samples

In some instances, the present disclosure relates to methods of detecting certain biomolecules in biofluid samples, the method including adding to biofluid samples certain compositions that include dextran sulphate (e.g., dextran sulphate having an average molecular weight of 726.6 g/mol) at the time the biofluid samples are obtained from subjects, or a period of time after the biofluid samples are obtained. In certain instances, the period of time between when the biofluid samples are obtained and when the compositions described herein are added to the biofluid samples is minimized, so that any degradation of the biomolecules in the biofluid samples is curtailed.

In some instances, the present disclosure relates to methods of improving detection of certain biomolecules in biofluid samples, the method including adding to biofluid samples certain compositions that include dextran sulphate (e.g., dextran sulphate having an average molecular weight of 726.6 g/mol) at the time the biofluid samples are obtained from subjects, or a period of time after the biofluid samples are obtained. In certain instances, the period of time between when the biofluid samples are obtained and when the compositions described herein are added to the biofluid samples is minimized, so that any degradation of the biomolecules in the biofluid samples is curtailed. For example, the method described herein can include collection of biofluid samples into a biofluid sample collection container that already contains an appropriate amount of a composition described herein, so that the biofluid samples mix with the composition as the biosamples are being collected.

In some instances, the detection is improved relative to a reference sample. In some instances, a "reference sample" (or "control" sample or the like) as used herein refers to a sample that does not express the biomolecule(s) (e.g., DNA, RNA). In some instances, the reference sample refers to a sample that expresses the bio biomolecule(s) (e.g., DNA, RNA) at a basal level. In some instances, a positive reference sample (i.e., a positive control sample) is used. A positive reference sample is a sample that expresses the biomolecule(s) (e.g., DNA, RNA). In some instances, a standard curve of samples with increasing or decreasing abundances (e.g., values) of positive reference samples. In some instances, the biomolecules (e.g., test or unknown biomolecules) can be measured compared to the standard curve.

In some instances, the compositions described herein can be added to biofluid samples within 30 seconds, 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 40 minutes, 50 minutes, 1 hour, 1.5 hour, 2 hours, 3 hours, 4 hours, 5 hours, 6 hours, 7 hours, 8 hours, 9 hours, 10 hours, 11 hours, 12 hours, 18 hours, 1 day, 2 days, 3 days, 4 days, 5 days, 6 days, or 1 week after obtaining the biofluid samples from subjects. In other instances, the compositions described herein can be added to biofluid samples after more than 30 seconds, 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 40 minutes, 50 minutes, 1 hour, 1.5 hour, 2 hours, 3 hours, 4 hours, 5 hours, 6 hours, 7 hours, 8 hours, 9 hours, 10 hours, 11 hours, 12 hours, 18 hours, 1 day, 2 days, 3 days, 4 days, 5 days, 6 days, or 1 week after obtaining the biofluid samples from subjects.

In some instances, the method described herein allows for the detection of specific biomolecules (e.g., specific DNA or RNA sequences) in biofluid samples a period of time after addition of any of the compositions described herein. For example, the specific biomolecules can be detected about 1 hour, 1.5 hour, 2 hours, 3 hours, 4 hours, 5 hours, 6 hours, 7 hours, 8 hours, 9 hours, 10 hours, 11 hours, 12 hours, 18 hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, or 5 years after the biofluid samples are obtained and/or any of the compositions described herein is added to biofluid samples.

In other instances, the specific biomolecules can be detected more than 1 hour, 1.5 hour, 2 hours, 3 hours, 4 hours, 5 hours, 6 hours, 7 hours, 8 hours, 9 hours, 10 hours, 11 hours, 12 hours, 18 hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, or 5 years after the biofluid samples are obtained and/or any of the compositions described herein is added to biofluid samples.

In other instances, the specific biomolecules can be detected less than 1 hour, 1.5 hour, 2 hours, 3 hours, 4 hours, 5 hours, 6 hours, 7 hours, 8 hours, 9 hours, 10 hours, 11 hours, 12 hours, 18 hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, or 5 years after the biofluid samples are obtained and/or any of the compositions described herein is added to biofluid samples.

In some instances, the method described herein can improve the detection of DNA or RNA in biofluid samples, as measured by % amount of DNA or RNA detected after a period of time, compared to the amount of DNA or RNA detected at time 0, where the % amount of DNA or RNA detected after 3 or 7 days is at least 50%, at least 60%, at least 70%, at least 80%, at least 90%, at least 95%, at least 96%, at least 97%, at least 98%, at least 99%, or greater than 100% of the amount of DNA or RNA that is detected at time 0. As described herein, the term "time 0" refers to between 0 and 2 hours after obtaining the biofluid sample.

In some instances, owing to improved stability of biomolecules (e.g., by inhibiting degradation or fragmentation of biomolecules) in biofluid samples when compositions described herein are added, the biofluid samples do not need to be stored at a lower temperature (e.g., 4° C.) or frozen (e.g., at <0° C.), but instead, can be stored without cooling (e.g., stored at an ambient temperature) before being analyzed. For example, in some embodiments, biofluid samples can be stored at a temperature that is greater than about 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C.

In some instances, the method described herein includes detection of biomolecules by any of the detection methods known in the art. For example, the presence of DNA having specific sequences can be detected by amplification of the DNA by polymerase chain reaction (PCR), Loop-mediated isothermal amplification (LAMP), Recombinase Polymerase Amplification (RPA), helicase-dependent isothermal DNA amplification (HDA), or other DNA amplification methods. DNA profiling can be performed by NGS, microarray, capillary sequencing, or by Southern blotting. As another example, the presence of RNA having specific sequences can be detected by a quantitative reverse-transcription PCR (e.g., qRT-PCR), capillary sequencing, fragment analysis, Next Generation Sequencing (NGS), or northern blotting. The presence of RNA having specific sequences can be detected with improved sensitivity and/or specificity by stabilizing the biomolecules in the biofluid samples.

In certain instances where the method includes an isothermal DNA amplification step (e.g., LAMP, RPA or HDA), biofluid samples can be prepared for the detection of biomolecules in containers in which the biosamples are collected. For example, cell lysis and target nucleic acid capture can occur in containers in which the biofluid samples are collected.

In certain instances, the presence of DNA having specific sequences can be detected using a signal amplification technique such as hybrid capture. For example, RNA probes specific for the target DNA can be used to create DNA-RNA hybrid, which is in turn recognized by an antibody specific for the DNA-RNA hybrid, and the antibody is detected by a sandwich ELISA type method.

In other instances, the presence of DNA having specific sequences can be detected using other signal amplification strategies such as branched DNA assay, or by using macroarrays containing immobilized detection probes to increase the level of multiplexing e.g. for detecting different subtypes of an infectious agent or different groups of conditions. The macroarrays can consist of a 2D layer of detection probes on a surface such as a flow cell or slide, or a 3D structure such as a hydrogel.

Diagnostic Application

The methods and compositions described herein can provide a number of advantages that enable temporally and logistically flexible collection, processing, and analysis of biofluid samples for the presence of biomolecules, owing to the improved detection of biomolecules in biofluid samples. Therefore, the collection and analysis process described herein can be adapted for various diagnostic applications.

In some embodiments, the methods described herein can be used to collect biofluid samples in a container that contains a composition described herein and can be transported to a laboratory for preparation of the biofluid samples for detection of biomolecules.

In other embodiments, the methods described herein can be used to collect biofluid samples in a container that contains a composition described herein, and the collected biofluid can be enriched for specific biomolecules, for example by immobilization of specific biomolecules on a surface (e.g., filter paper, or an activated surface), and the immobilized biomolecules can be transported to a laboratory for detection of biomolecules. Such enrichment of specific biomolecules can enable collection of larger volumes of biofluid samples from which the specific biomolecules can be enriched, so that a greater amount of biomolecules can be collected from a subject.

In another embodiment, the methods described herein can be used to collect biofluid samples in a container, and the processing step (e.g., purification, separation, and amplification of biomolecules) and detection step can be performed in a single device. In such instances, the biomolecules in a biofluid sample can be amplified isothermally in the device that the biofluid sample is collected.

Diagnosis and/or Monitoring of Conditions and Diseases

In some instances, the present disclosure relates to diagnosis and/or monitoring of various conditions and/or diseases by detecting the presence of specific biomolecules (e.g., DNA or RNA), which are associated with specific conditions or diseases.

In instances where the biofluid sample is urine, compositions described herein can be added to urine to improve the detection of RNA and/or DNA in urine. For example, detection of specific DNA or RNA that are associated with sexually transmitted diseases, or infections involving the genital tract, urinary tract, kidney, or bladder can be improved by the addition of compositions described herein to urine.

For example, detection of DNA or RNA having sequences specific for an infectious agent (e.g., a virus, bacteria, or fungus) in urine samples can indicate an infection. In certain instances, the infectious agent can be a virus such as Herpesvirus (Herpes simplex Viruses 1 and 2, Varicella zoster virus, Human herpes virus-6, Human herpes virus-7, Human herpes virus-8, Epstein barr virus), Adenovirus, Cytomegalovirus, Human papilloma virus, Enterovirus, Zika virus, Polyomaviruses such as BK virus, Coxsackie A viruses, Hepatitis viruses, Arbovirus, Parvovirus B19, Reovirus, Measles virus, Gastrointestinal viruses, Influenza, Parainfluenza, Mumps, Respiratory syncytial virus, Coronaviruses, Enteroviruses, Hemorrhagic fever viruses (such as Congo-Crimean hemorrhagic fever, Ebola virus, Hantavirus, Dengue, chikungunya, West Nile virus, Nipah virus, Yellow fever virus, Hepatitis A, Hepatitis B, Hepatitis C, Noroviruses, Rabies, Rhinovirus, or Birnaviruses (rotaviruses).

In some embodiments, the virus is a coronavirus. In some instances, the virus is SARS-CoV-1. In some instances, the virus is SARS-CoV-2. In some instances, the virus is Middle East Respiratory Syndrome (MERS).

In some embodiments, the bacteria is Mycobacteria, *Serratia, Staphylococcus, Streptococcus, Klebsiella, Escherechia, Neisseria, Shigella, Salmonella, Helicobacteria, Listeria, Morganella, Pseudomonas, Acinetobacter, Bacteroides, Burkholderia, Clostridium, Enterobacteriaceae, Enterococcus, Stenotrophomonas.*

In some embodiments, the fungus described herein is Entomophtoromycota (such as *Basidiobolus* and *Conidiobolus*), Ascomycota (such as *Candida, Aspergillus,* Non-*Fumigatus* Aspergilli, *Fusarium,* Pseudoallescheria, and Other Opportunistic, Ascomycetous Fungal Pathogens such as *Blastomyces, Pneumocystis*), Basidiomycota (such as Cryptococci), Mucorales (such as *Mucor* and *Rhizopus*), or *Histoplasma.*

For another example, detection of DNA or RNA having specific gene mutations can indicate the presence or increased risk of developing cancer. For example, DNA or RNA having gene mutations in the BRCA1, BRCA2, HOXB13, or ATM genes can indicate the presence or increased risk of developing prostate cancer.

Diagnosis and/or Monitoring of HPV Infection

HPV infection is a prevalent sexually transmitted condition that can lead to warts and cancers. Over 40 different subtypes of sexually transmitted HPVs exist, and these different types of HPV can result in different clinical outcomes, such as cancer or genital warts. For example, HPV-16 and HPV-18 are known to be responsible for 70% of all cervical cancers, whereas HPV-6 and HPV-11 are known to cause 90% of all genital warts.

Although screening for HPV infection is of great interest to public health, presently, diagnosis of HPV infection often involves intrusive, uncomfortable, and invasive procedures such as pap tests, colposcopy, biopsy, which requires visits to clinics or hospitals or intervention by those who are specially trained (e.g., doctors or nurses).

In certain instances, the present disclosure relates to diagnosis and/or monitoring of HPV infection by detecting the presence of specific DNA or RNA having sequences associated with HPV in urine samples as a surrogate for HPV infection (e.g., of the genital tract). Such methods can provide sensitive and consistent detection of DNA or RNA sequences specific for different types, subtypes, or subspecies of HPV, thereby providing information about the potential development of specific clinical symptoms or outcomes associated with the HPV types, subtypes, or subspecies (e.g., cancer or genital warts).

Methods of Treating Subjects for Conditions or Diseases

In certain instances, the present disclosure relates to treating subjects for conditions or diseases, where the method of detecting biomolecules described herein provides diagnosis for certain conditions or diseases.

For example, biofluid samples can be obtained from subjects, to which compositions described herein can be added to improve detection of biomolecules such as DNA or RNA. Next, various detection methods (e.g., NGS or RT-PCR) can be used to detect the presence of specific biomolecules that are associated with certain conditions or diseases, thereby providing diagnosis for the conditions or diseases. Once certain conditions or diseases have been diagnosed in the subjects, appropriate treatment can be administered to the subject based on the diagnosis, such as administration of antibiotics or antiviral agents to treat infections, or chemotherapy, radiation therapy, immunotherapy, and/or surgery to treat cancer.

EXAMPLES

The disclosure is further described in the following examples, which do not limit the scope of the disclosure described in the claims.

Example 1: Improved Detection of DNA in Urine by Formulation 1

Figure 2:
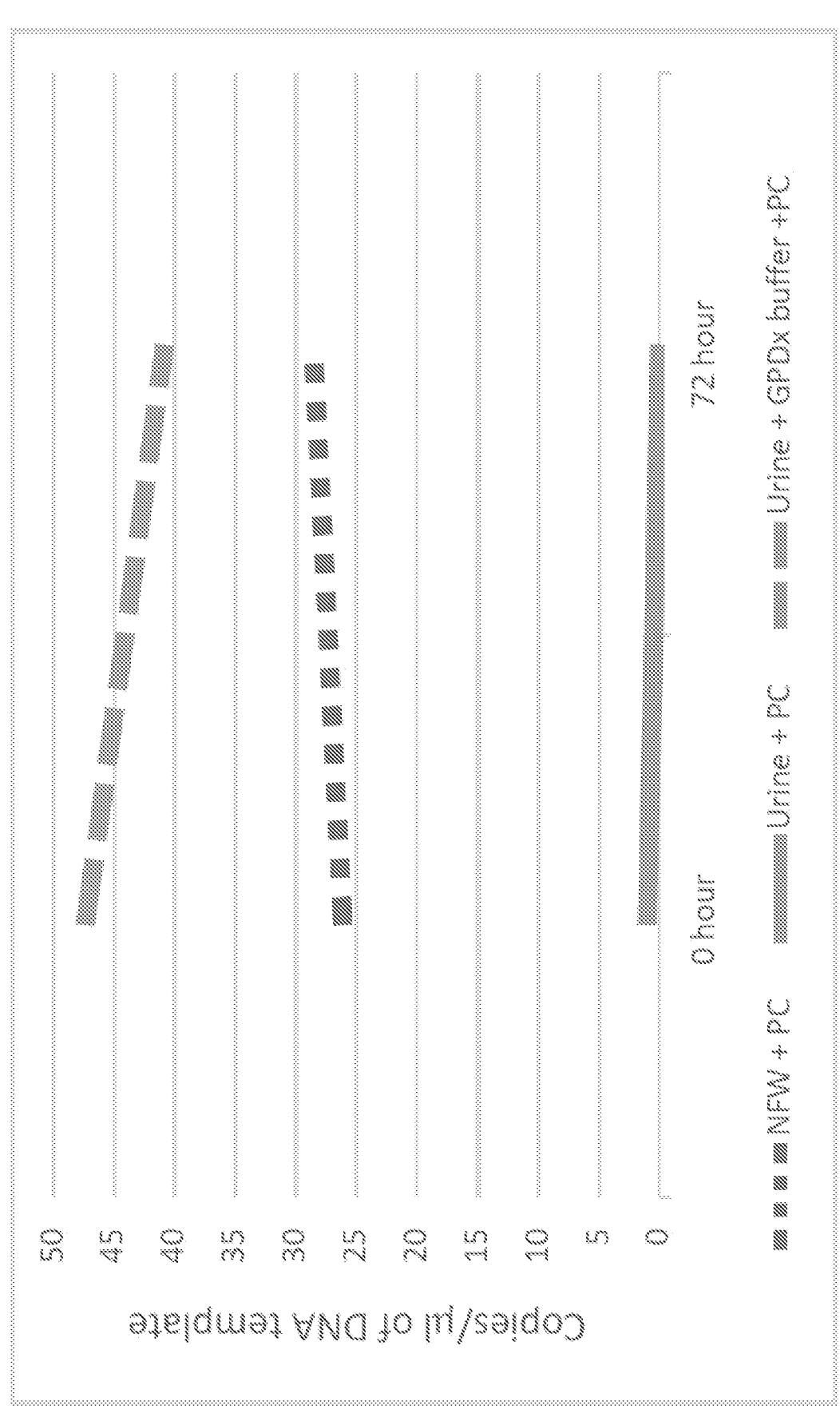
FIG. 2 is a line graph showing the effects of adding Formulation A solution (indicated as GPDx) to urine samples on detection of DNA in the urine samples after 72 hours.

The formulation described below were used to improve detection of DNA in urine samples. FIGS. 1 and 2 show the extent of improvements in DNA detection in urine samples when Formulation 1 described below is added.

Formulation 1:

Contains components sufficient to provide a final concentration of the following:

80 mM Tris-HCl (pH 7.0)

4 mM EDTA (ethylenediaminetetraacetic acid)

40 mM boric acid 40 mM sodium citrate 500 nM dextran sulphate (e.g., 726.6 g/mol)

10 mM lithium chloride

Experimental Protocol:

For these experiments, an equal amount of CMV-positive plasma was spiked in three sets of two tubes, each set containing:

Only nuclease-free water;

Urine; or

Urine and working concentration of Formulation 1.

Viral nucleic acid extraction was performed immediately for one set ("0-hour") and the other set was stored at room temperature for 3 days (72 hours). The extraction was performed using the Qiagen minelute kit as per the protocol and eluted in a volume of 35 µl. 5 µl of this extracted DNA was used as the input for an in-house CMV quantitative real-time PCR.

As shown in FIGS. 1 and 2, detection of DNA was significantly improved at both time 0 (indicated as "0 hour" to indicate assaying samples at less than 2 hours after obtaining biofluid samples) and at 72 hours after obtaining urine samples in the test samples that contained Formulation 1 (indicated as "GPDx") (added within 1 hour of obtaining urine samples), as compared to urine samples or distilled water control where Formulation 1 was not added. The low detection level of DNA in urine sample without Formulation 1, even at time 0 ("0 hour") can be attributed to the rapid degradation of DNA in urine that occur during the short time period (approximately 1 hour) between when the urine sample is collected and when DNA detection assay is performed.

Example 2: Comparison of Formulation 1 and Commercially Available Urine Buffers The commercial buffers against which we compared our buffer were:

Urine Conditioning buffer by Zymo Research

Urine Preservation Buffer by NorgenTek

Cell-free DNA Urine preserve by Streck

HeLa cells, which are immortalized cervical cancer cells, contain the HPV16 genome in addition to the human genome. Therefore, spiking urine samples with HeLa cells provide a good surrogate for urine samples of subjects having HPV infections (e.g., of the genital tract). We compared the efficacy of the GPDx Urine buffer against that of other currently available buffers. Quantitative PCRs was performed to measure HPV specific DNA by measuring a HPV-specific sequence and a human housekeeping gene, as described below.

For both Streck and NorgenTek buffers, the entire contents of the buffer ampoule were emptied into a 50-ml tube. The volume was made up to 25 ml with Urine.

For the zymo buffer, 70 ul of the buffer was added to 1 ml of Urine.

For Formulation 1, the urine was diluted 1:10 in the buffer to result in the desired concentration of constituents of Formulation 1 after dilution.

$5 \times 10^4$ HeLa were spiked into each buffer and urine mix.

200 µl of each mix was aliquotted in 1.5-ml tubes and these were used for each time-point extraction.

The extraction was performed using the Qiagen minelute kit as per the protocol and eluted in a volume of 35 µl.

After extraction DNA from urine samples after 0-, 3-, and 7-day time points, qPCRS were performed for HPV (GP5+/6+SYBR PCR) and a human housekeeping gene (RNaseP) using published primers from literature. The PCRs for all time-points were performed in the same PCR run.

Figure 3:
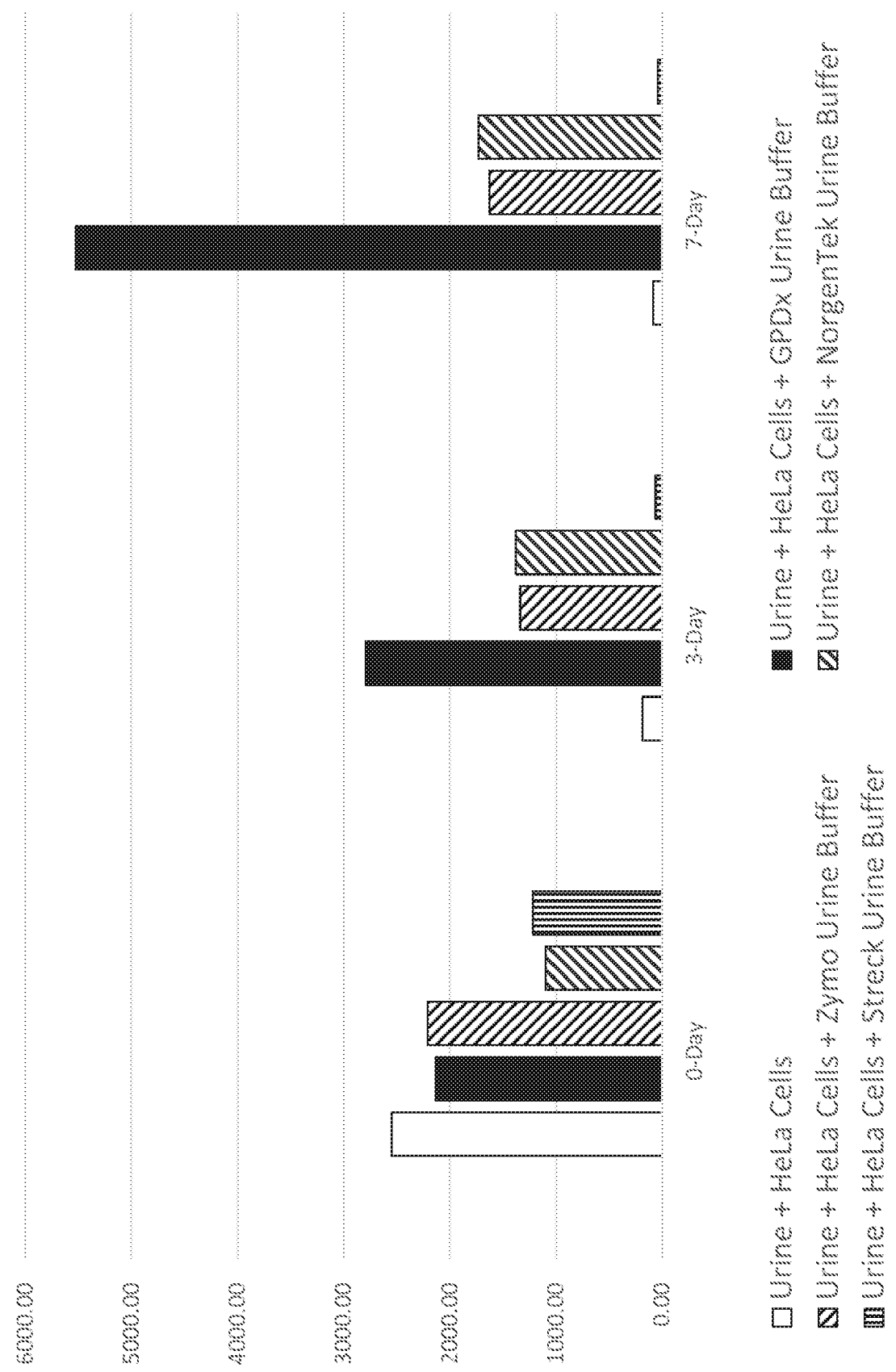
FIG. 3 is a bar graph showing comparative improvements in DNA detection in urine between Formulation A and other commercially available buffers (Zymo buffer, NorgenTek buffer, and Strek buffer) at various time points over a 7-day period.
Figure 4:
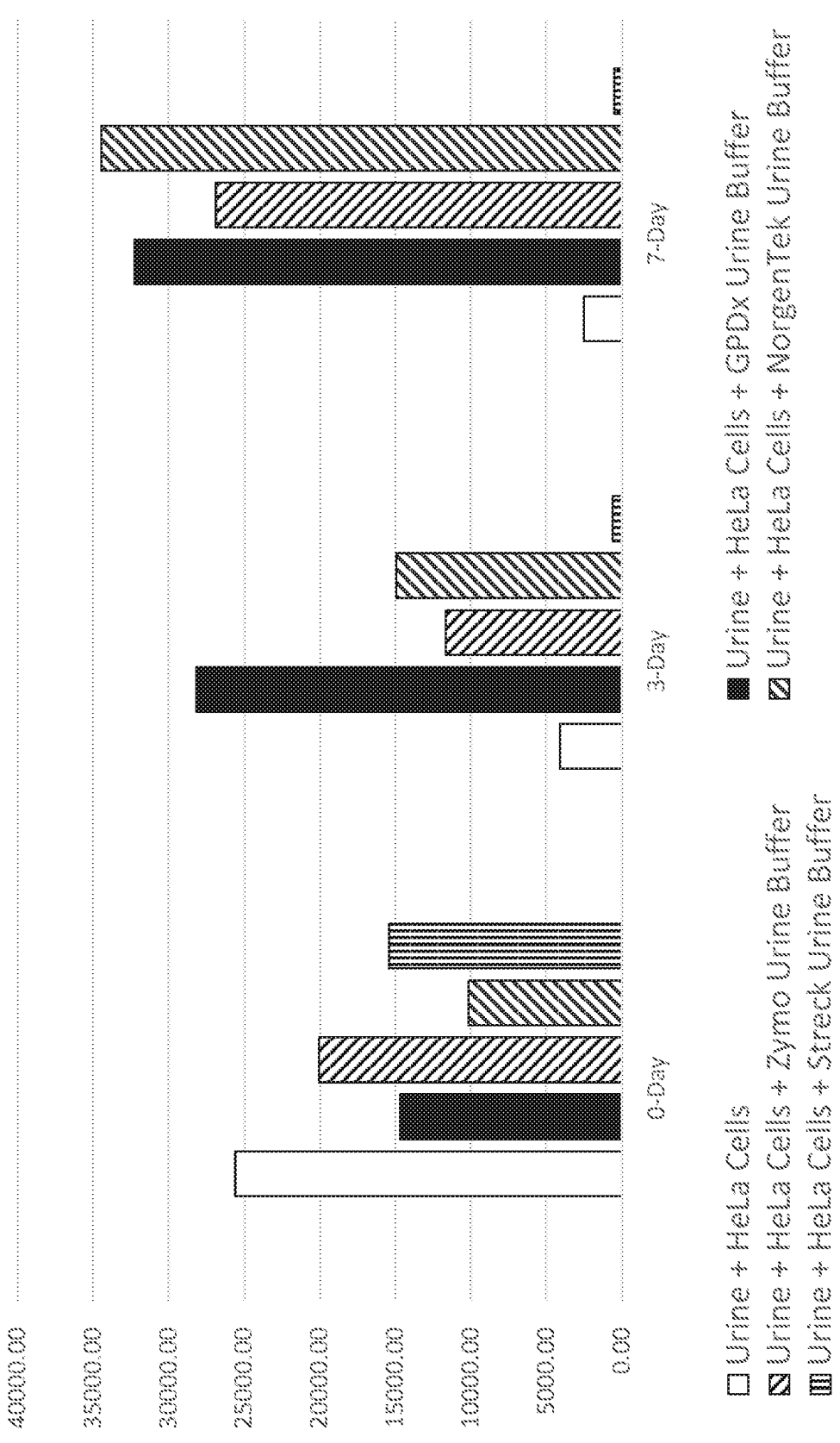
FIG. 4 is a bar graph showing the effects of Formulation A, Zymo buffer, NorgenTek buffer, and Strek buffer on detection of DNA in urine samples over a 7-day period.

As shown in FIGS. 3 and 4, detection of DNA in urine samples is improved when Formulation 1 is added to urine samples, as compared to urine samples containing other commercially available urine buffers (indicated as "Zymo Urine Buffer", "Streck Urine Buffer", and "NorgenTek Urine Buffer") or to control urine samples that do not contain any buffer additives. The detection of DNA in urine samples improves over time (higher DNA detection levels in 3-day v. 0-day, and in 7-day v. 3-day) when Formulation 1 is added to the urine sample.

Example 3: Another Example of Composition for Improving Detection of DNA in Urine The composition described herein can include additional components (e.g., aurintricarboxylic acid, polyvinylpyrrolidone, and/or Tris (2-carboxylethyl) phosphine) in addition to the components included in Formulation 1, described above. Some of the additional components (e.g., Polyvinylpyrrolidone) can provide improved DNA stabilization and/or biofluid sample preservation in situations where the biofluid sample contains fecal contaminants. Formulation 2, described below, can also be added to urine samples to improve DNA or RNA detection, especially when the urine contains fecal contaminants, or is suspected of containing fecal contaminants.

Formulation 2:

Contains components sufficient to provide a final concentration of the following:

80 mM Tris-HCl (pH 7.0)

4 mM EDTA (ethylenediaminetetraacetic acid)

40 mM boric acid 40 mM sodium citrate 500 nM dextran sulphate 10 mM lithium chloride 10 mM Aurintricarboxylic acid 0.25% (w/v) Polyvinylpyrrolidone 500 nM Tris (2-carboxylethyl) phosphine

Example 4: Use of Formulation 1 or Formulation 2 in Diagnosis of HPV Infection Formulation 1 or Formulation 2 described above will be placed in a container such that Formulation 1 or Formulation 2 will mix with urine sample that is placed in the container. Collection of urine in the container will be done by the subject (e.g., at subject's home), or at a healthcare facility (e.g., at a clinic or hospital) and sent to a laboratory for analysis.

DNA and/or RNA in the urine sample will be enriched by cell lysis and DNA and/or RNA prep, and sequence of interest will be amplified by PCR/RT-PCR using primers that are specific for portions of the L1 or E6/E7 genes of one or more HPV types, and detected, or by whole genome sequencing using random primers. To improve detection, the sequence-specific amplification or whole genome sequencing step can be preceded by a pre-amplification step (e.g., whole genome amplification using enzymes such as phi29 with exoresistant primers (e.g., phosphorothioated primers) or by in situ primers synthesized by primases. The pre-amplification step also can include whole transcriptome reverse-transcription to cDNA using reverse-transcriptases.

The nucleic acid amplification step will be performed using isothermal methods such as LAMP, HAD, RPA. The nucleic amplification step may include use of modified nucleotides, primers containing artificial nucleotides (e.g., SAMRS or AEGISP) and 'hotstart' nucleotides. Alternatively, the nucleic acid amplification step will be performed using hybrid capture, where a DNA-RNA hybrid is formed using an RNA probe that is specific for the target DNA sequence, and an antibody that recognizes the DNA-RNA hybrid is used to bind to the DNA-RNA hybrid and detected using a sandwich ELISA method. The detection of amplified signal is alternatively be performed macro-array method where detection probes to detect for multiple subtypes/subspecies of HPV. The macroarrays may consist of a 2D layer of detection probes on a surface such as a flow cell or slide, or a 3D structure such as a hydrogel.

The results of the urine sample analysis will be used to: (1) recommend further diagnosis (e.g., confirmatory diagnosis such as cervical/vaginal swab, cytology based assays); (2) to recommend treatment options to a doctor or a healthcare professional; or (3) record in a medical record for the subject, so that appropriate treatment can be administered to the subject.

Example 5: Use of Formulation 1 or Formulation 2 in Diagnosis of HPV Infection Using Point-of-Care Compatible Diagnosis Assay The methods described in Example 4, above, will be adapted for point-of-care diagnostic assay, where the detection of specific sequences of nucleic acid in the biofluid sample can be conducted where the biofluid sample is collected (e.g., at a subject's home or a clinic) without the need for transporting the biofluid sample to a laboratory facility for analysis.

The sequences of interest (DNA or cDNA reverse transcribed from RNA) will be amplified by isothermal methods like (RT) LAMP, HDA or RPA. Preamplification using whole genome amplification (with enzymes like phi29 and its derivatives) and reverse transcription may be carried out to further improve detection sensitivity.

Reverse transcription may be primed using random primers which may incorporate non-natural bases such as SAMRS and AEGIS. Detection may be carried out by a real-time chemistry like intercalating dyes, hydrolysis probes, molecular beacons, etc. Multiplexing may be increased by incorporating the reporter molecules into geographically separated regions through constructs like hydrogels thereby reducing the need for multiple fluorescent reporters with discrete fluorescence spectra, and circumventing the limitations of multiplexing.

Example 6: Use of Formulation 1 or Formulation 2 in Diagnosis of HPV Infection Using Integrated Point-of-Care Compatible Diagnosis Assay The method described in Examples 4 and 5, above, will further be adapted for an integrated point-of-care diagnostic assay where a single device can handle both the collection and processing of a biofluid sample and/or processing and detection for the presence of specific nucleic acid sequences in the biofluid sample.

The device will be configured such that a user (e.g., the subject who is providing the biofuid sample) or a healthcare provider can operate the device to process the biofluid sample for analysis, and/or obtain information regarding the presence and/or the relative abundance of nucleic acids (e.g., DNA and/or RNA) having specific sequences associated with HPV infection.

The device will include (1) a microfluidics component that allows flowing and processing of cells; (2) cartridge component that can process biofluid samples; and/or (3) a sequence detection system that includes RNA probes complimentary to different genotypes of the virus immobilized on a surface or in a 3D structure such as a hydrogel, where the biofluid sample containing HPV DNA will be contacted with these hydrogels, and if complementary sequences are present, they would bind to the cognate immobilized probe.

Example 7: Use of Formulation 1 or Formulation 2 in Diagnosis of SARS-CoV-2 Infection Formulation 1 or Formulation 2 described above will be placed in a container such that Formulation 1 or Formulation 2 will mix with a saliva or nasal swab sample that is placed in the container. Collection of the saliva or nasal swab sample in the container will be done by the subject (e.g., at subject's home), or at a healthcare facility (e.g., at a clinic or hospital) and sent to a laboratory for analysis.

DNA and/or RNA in the saliva or nasal swab sample will be enriched by cell lysis and DNA and/or RNA prep, and sequence of interest will be amplified by PCR/RT-PCR using primers that are specific for portions of the SARS-CoV-2 virus, and detected, or by whole genome sequencing using random primers. To improve detection, the sequence-specific amplification or whole genome sequencing step can be preceded by a pre-amplification step (e.g., whole genome amplification using enzymes such as phi29 with exoresistant primers (e.g., phosphorothioated primers) or by in situ primers synthesized by primases. The pre-amplification step also can include whole trascriptome reverse-transcription to cDNA using reverse-transcriptases.

The nucleic acid amplification step is performed using isothermal methods such as LAMP, HAD, RPA. The nucleic amplification step includes use of modified nucleotides, primers containing artificial nucleotides (e.g., SAMRS or AEGISP) and 'hotstart' nucleotides. Alternatively, the nucleic acid amplification step will be performed using hybrid capture, where a DNA-RNA hybrid is formed using an RNA probe that is specific for the target DNA sequence, and an antibody that recognizes the DNA-RNA hybrid is used to bind to the DNA-RNA hybrid and detected using a sandwich ELISA method. The detection of amplified signal is alternatively performed macro-array method where detection probes to detect for multiple subtypes/subspecies of SARS-CoV-2. The macroarrays may consist of a 2D layer of detection probes on a surface such as a flow cell or slide, or a 3D structure such as a hydrogel.

The results of the urine sample analysis are used to: (1) recommend further diagnosis; (2) to recommend treatment options to a doctor or a healthcare professional; or (3) record in a medical record for the subject, so that appropriate treatment can be administered to the subject.

Example 8: Use of Formulation 1 or Formulation 2 in Diagnosis of SARS-CoV-2 Infection Using Point-of-Care Compatible Diagnosis Assay The methods described in Example 4, above, are adapted for point-of-care diagnostic assay, where the detection of specific sequences of nucleic acid in the biofluid sample can be conducted where the biofluid sample is collected (e.g., at a subject's home or a clinic) without the need for transporting the biofluid sample to a laboratory facility for analysis.

The sequences of interest (DNA or cDNA reverse transcribed from RNA) will be amplified by isothermal methods like (RT) LAMP, HDA or RPA. Preamplification using whole genome amplification (with enzymes like phi29 and its derivatives) and reverse transcription may be carried out to further improve detection sensitivity.

Reverse transcription may be primed using random primers which may incorporate non-natural bases such as SAMRS and AEGIS. Detection may be carried out by a real-time chemistry like intercalating dyes, hydrolysis probes, molecular beacons, etc. Multiplexing may be increased by incorporating the reporter molecules into geographically separated regions through constructs like hydrogels thereby reducing the need for multiple fluorescent reporters with discrete fluorescence spectra, and circumventing the limitations of multiplexing.

Example 9: Use of Formulation 1 or Formulation 2 in Diagnosis of SARS-CoV-2 Infection Using Integrated Point-of-Care Compatible Diagnosis Assay The method described in Examples 4 and 5, above, are further adapted for an integrated point-of-care diagnostic assay where a single device can handle both the collection and processing of a biofluid sample and/or processing and detection for the presence of specific nucleic acid sequences in the biofluid sample.

The device will be configured such that a user (e.g., the subject who is providing the biofuid sample) or a healthcare provider can operate the device to process the biofluid sample for analysis, and/or obtain information regarding the presence and/or the relative abundance of nucleic acids (e.g., DNA and/or RNA) having specific sequences associated with HPV infection.

The device will include (1) a microfluidics component that allows flowing and processing of cells; (2) cartridge component that can process biofluid samples; and/or (3) a sequence detection system that includes RNA probes complimentary to different genotypes of the virus immobilized on a surface or in a 3D structure such as a hydrogel, where the biofluid sample containing HPV DNA will be contacted with these hydrogels, and if complementary sequences are present, they would bind to the cognate immobilized probe.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of detecting a nucleic acid in a biofluid sample, the method comprising:
   (a) adding to the biofluid sample a composition comprising:
       (i) a sufficient amount of dextran sulphate to provide between 50 nM and 5 µM dextran sulphate when the composition is added to the biofluid sample;
       (ii) a buffer agent comprising a sufficient amount of Tris-HCl (pH 7.0) to provide between 8 mM and 800 mM Tris-HCl (pH 7.0) when the composition is added to the biofluid sample;
       (iii) a chelating agent comprising a sufficient amount of ethylenediaminetetraacetic acid (EDTA) to provide between 0.4 mM and 40 mM EDTA when the composition is added to the biofluid sample;
       (iv) a sufficient amount of boric acid to provide between 4 mM and 400 mM boric acid when the composition is added to the biofluid sample;
       (v) a sufficient amount of sodium citrate to provide between 4 mM and 400 mM sodium citrate when the composition is added to the biofluid sample; and
       (vi) a sufficient amount of lithium chloride to provide between 1 mM and 100 mM lithium chloride when the composition is added to the biofluid sample; and
   (b) detecting the nucleic acid by polymerase chain reaction (PCR), loop-mediated isothermal amplification (LAMP), recombinase polymerase amplification (RPA), helicase-dependent isothermal DNA amplification (HDA), Southern blotting, quantitative reverse-transcription PCR, capillary sequencing, fragment analysis, Next Generation Sequencing (NGS), or Northern blotting.

2. The method of claim 1, wherein the detection is increased relative to a reference sample.

3. The method of claim 1, wherein the composition comprises:
   a. a sufficient amount of Tris-HCl (pH 7.0) to provide about 80 mM Tris-HCl (pH 7.0) when the composition is added to the biofluid sample;
   b. a sufficient amount of EDTA to provide about 4 mM EDTA when the composition is added to the biofluid sample;
   c. a sufficient amount of boric acid to provide about 40 mM boric acid when the composition is added to the biofluid sample;
   d. a sufficient amount of sodium citrate to provide about 40 mM sodium citrate when the composition is added to the biofluid sample;

e. a sufficient amount of dextran sulphate to provide about 500 nM dextran sulphate when the composition is added to the biofluid sample; and
   f. a sufficient amount of lithium chloride to provide about 10 mM lithium chloride when the composition is added to the biofluid sample.

4. The method of claim 1, wherein the composition further comprises:
   a. a sufficient amount of aurintricarboxylic acid to provide between 1 mM and 100 mM aurintricarboxylic acid when the composition is added to the biofluid sample;
   b. a sufficient amount of polyvinylpyrrolidone to provide between 0.01% and 10% (w/v) polyvinylpyrrolidone when the composition is added to the biofluid sample; and
   c. a sufficient amount of Tris (2-carboxylethyl) phosphine to provide between 100 nM and 1 µM Tris (2-carboxylethyl) phosphine when the composition is added to the biofluid sample.

5. The method of claim 4, wherein the composition comprises:
   a. a sufficient amount of aurintricarboxylic acid to provide about 10 mM aurintricarboxylic acid when the composition is added to the biofluid sample;
   b. a sufficient amount of polyvinylpyrrolidone to provide about 0.25% (w/v) polyvinylpyrrolidone when the composition is added to the biofluid sample; and
   c. a sufficient amount of Tris (2-carboxylethyl) phosphine to provide about 500 nM Tris (2-carboxylethyl) phosphine when the composition is added to the biofluid sample.

6. The method of claim 1, wherein the biofluid sample is urine or wherein the biofluid sample comprises fecal containment.

7. The method of claim 1, wherein the composition is powder, a tablet, a gel, or an aqueous solution.

8. The method of claim 1, wherein the nucleic acid comprises one or more target DNA or RNA sequence(s) of an infectious agent selected from a virus, a bacteria, or a fungus.

9. The method of claim 8, wherein the virus is Herpesviridae, Epstein barr virus, Adenovirus, Cytomegalovirus, Human papilloma virus, Enterovirus, Zika virus, Polyomaviruses such as BK virus, Coxsackie A viruses, Hepatitis viruses, Arbovirus, Parvovirus B19, Reovirus, Measles virus, Gastrointestinal viruses, Influenza, Parainfluenza, Mumps, Respiratory syncytial virus, Adenoviruses, Coronaviruses, Enteroviruses, Hemorrhagic fever viruses, Ebola virus, Hantavirus, Dengue, chikungunya, West Nile virus, Nipah virus, Yellow fever virus, Hepatitis A, Hepatitis B, Hepatitis C, Noroviruses, Rabies, Rhinovirus, Birnaviruses (rotaviruses) SARS-COV-1, SARS-COV-2, or Middle East Respiratory Syndrome (MERS).

10. The method of claim 9, wherein the virus is SARS-COV-2.

* * * * *